United States Patent
Diamond et al.

(10) Patent No.: US 10,496,893 B2
(45) Date of Patent: Dec. 3, 2019

(54) HANDHELD ARTHROPOD DETECTION DEVICE

(71) Applicant: DiamondFox Enterprises, LLC, Baltimore, MD (US)

(72) Inventors: Paul T. Diamond, Crozet, VA (US); Margie Fox Kwart, Baltimore, MD (US); Beau Tippetts, Provo, UT (US)

(73) Assignee: DiamondFox Enterprises, LLC, Baltimore, MD (US)

( * ) Notice: Subject to any disclaimer, the term of this patent is extended or adjusted under 35 U.S.C. 154(b) by 203 days.

(21) Appl. No.: 15/673,389

(22) Filed: Aug. 9, 2017

(65) Prior Publication Data

US 2018/0046872 A1      Feb. 15, 2018

Related U.S. Application Data

(60) Provisional application No. 62/373,578, filed on Aug. 11, 2016.

(51) Int. Cl.
*G06K 9/00* (2006.01)
*G06K 9/22* (2006.01)
(Continued)

(52) U.S. Cl.
CPC ......... *G06K 9/228* (2013.01); *G06K 9/00369* (2013.01); *G06K 9/00671* (2013.01);
(Continued)

(58) Field of Classification Search
CPC ............... G06K 9/228; G06K 9/00369; G06K 9/00671; G06K 9/3233; G16H 30/40;
(Continued)

(56) References Cited

U.S. PATENT DOCUMENTS

| 5,997,846 A | 12/1999 | Burns et al. |
| 2005/0168336 A1 | 8/2005 | Donskoy et al. |

(Continued)

FOREIGN PATENT DOCUMENTS

| CN | 104213232 A | 12/2014 |
| CN | 204832052 U | 12/2015 |

(Continued)

OTHER PUBLICATIONS

International Preliminary Report on Patentability of the International Application No. PCT/US2017/046577, dated Feb. 21, 2019, 10 pages.

(Continued)

*Primary Examiner* — Andrew M Moyer
(74) *Attorney, Agent, or Firm* — The Marbury Law Group, PLLC

(57) ABSTRACT

Various embodiments include systems and methods of arthropod detection using an electronic arthropod detection device. A processor of an electronic arthropod detection device may scan a surface or a subject using the electronic arthropod detection device and capture at least one image while scanning the surface or the subject using the electronic arthropod detection device. The processor may determine whether the at least one image includes a region of interest (ROI) corresponding to an arthropod and provide an identification area of the at least one image to an object detection model in response to determining that the at least one image includes an ROI. The processor may initiate an arthropod detected procedure in response to receiving a result from the object detection model that indicates that an arthropod is detected within the identification area of the at least one image.

18 Claims, 19 Drawing Sheets

(51) Int. Cl.

| | | |
|---|---|---|
| G06K 9/32 | (2006.01) | |
| H04N 5/33 | (2006.01) | |
| G16H 30/40 | (2018.01) | |
| G16H 40/63 | (2018.01) | |
| G06F 19/00 | (2018.01) | |

(52) U.S. Cl.
CPC ............ *G06K 9/3233* (2013.01); *G16H 30/40* (2018.01); *G16H 40/63* (2018.01); *H04N 5/33* (2013.01); *G06F 19/321* (2013.01); *G06F 19/325* (2013.01); *Y02A 90/26* (2018.01)

(58) Field of Classification Search
CPC .......... G16H 40/63; H04N 5/33; Y02A 90/26; G06F 19/321; G06F 19/325
USPC ........................................................ 382/103
See application file for complete search history.

(56) References Cited

U.S. PATENT DOCUMENTS

| | | | |
|---|---|---|---|
| 2009/0122164 A1 | 5/2009 | Maki et al. | |
| 2009/0153659 A1* | 6/2009 | Landwehr ............. | A01M 1/026 348/135 |
| 2011/0225873 A1 | 9/2011 | McKnight et al. | |
| 2012/0137569 A1* | 6/2012 | Younts .................. | A01M 1/026 43/139 |
| 2013/0011011 A1 | 1/2013 | Fryshman | |
| 2014/0311014 A1 | 10/2014 | Feugier | |
| 2015/0121745 A1 | 5/2015 | Borth et al. | |
| 2015/0148685 A1 | 5/2015 | Baym et al. | |
| 2016/0018885 A1 | 1/2016 | Kimura et al. | |
| 2017/0185276 A1* | 6/2017 | Lee ..................... | G06F 3/04847 |

FOREIGN PATENT DOCUMENTS

| | | | |
|---|---|---|---|
| EP | 1936518 B1 | 6/2011 | |
| WO | WO9966790 A1 | 12/1999 | |
| WO | WO2012058239 A1 | 5/2012 | |
| WO | WO2013000028 A1 | 1/2013 | |
| WO | WO2013096341 A1 | 6/2013 | |
| WO | WO2014/125158 A1 * | 8/2014 | ............... G06T 7/00 |

OTHER PUBLICATIONS

Wakefield, M. E., "Storage arthropod pest detection—current status and future directions," pp. 371-384, viewed on Nov. 6, 2017, http://citeseerx.ist.psu.edu/viewdoc/download?doi=10.1.1.598.8788&rep=rep1&type=pdf.
"The Tick Detective," viewed on Nov. 6, 2017, http://nstawebdirector.wixsite.com/thetickdetective.
"Tick Comb Illuminated Comb Review—A Fantastic Product to Detect Ticks Fast," Viewed on Nov. 6, 2017, https://www.tickbites.net/tick-comb-illuminated-comb-review/.
CDC, Centers for Disease Control and Prevention, "Stop Ticks," Viewed on Nov. 6, 2017, https://www.cdc.gov/features/stopticks/index.html.
Mass.Gov, "Health and Human Services: Personal Protection Against Ticks," Viewed on Nov. 6, 2017, http://www.mass.gov/eohhs/gov/departments/dph/programs/id/epidemiology/ticks/ticks-personal-protection.html.
Wright, M., "How to Tell If You Have a Tick," Healthfully, Viewed on Nov. 6, 2017, https://healthfully.com/tell-tick-5668542.html.
"How to Tick Check Yourself," Viewed on Nov. 6, 2017, https://aftergadget.wordpress.com/2011/10/04/how-to-tick-check-yourself/.
Hollingshead, T., "BYU's smart object recognition algorithm doesn't need humans," Jan. 14, 2014, https://news.byu.edu/news/byus-smart-object-recognition-algorithm-doesnt-need-humans.
Arthropods of Our Homes, "Guide to Common Insects and Other Arthropods Found in and Around North Carolina Homes," Viewed Nov. 6, 2017, http://robdunnlab.com/wp-content/uploads/Final_AOHGuide.pdf.
NEC, ""Insect Identification Support Service" using image recognition technology," Viewed on Nov. 6, 2017, http://www.nec.com/en/global/eco/life/it/identified_insects.html.
University of Rhode Island, "TickEncounter Resource Center," Viewed on Nov. 6, 2017, http://www.tickencounter.org/tick_identification.
Yang, H. et al., "Research on insect identification based on pattern recognition technology," Conference: Sixth International Conference on Natural Computation, ICNC 2010, Yantai, Shandong, China, Aug. 10-12, 2010, https://www.researchgate.net/publication/221162395_Research_on_insect_identification_based_on_pattern_recognition_technology.
Parola, P. et al., "Ticks and Tickborne Bacterial Diseases in Humans: An Emerging Infectious Threat," Clinical Infectious Diseases, vol. 32, Issue 6, Mar. 15, 2001, pp. 897-928.
CDC, Centers for Disease Control and Prevention, "Tickborne Diseases of the United States," Viewed on Nov. 6, 2017, https://www.cdc.gov/ticks/diseases/index.html.
CDC, Centers for Disease Control and Prevention, "Data and Statistics," Viewed on Nov. 6, 2017, https://www.cdc.gov/lyme/stats/index.html.
FLIR, "FLIR Thermal Imaging Cameras Reveal the Secrets of Coexisting Insects," Research & Science, Nov. 5, 2015 http://www.flir.com/science/blog/details/index.cfm?ID=72021.
Williams, J. D., "Flea Detector Comb," Sep. 21, 2016, 2 pages.
Nix, "Electronic Lice Comb," INSIGHT Pharmaceuticals, Corp., Trevose, PA 19053 © 2013, 61-16-363A nixlice.com.
"Patentability Search Report," Effectual Services, Innovating Solutions to Support Your Goals, The Handheld Arthropod Detection Wand, 49 pages, Sep. 22, 2016.
"Termatrac: The World's No. 1 Termite Detector," 3 in 1 Termite Detection Tool, 1 page, Sep. 21, 2016.
Pests.guru, "Useful Equipment: Termite Detection Tools," Termite Detection Tools: Imaging Camera Device and Other Systems for Searching Pests, Sep. 21, 2016, http://pests.guru/termites/sign-of-infestation/check-for-termites/detection-tools.html.
Barbedo, J. G., et al., "The Use of Infrared Images to Detect Ticks in Cattle and Proposal of an Algorithm for Quantifying the Infestation," Vet Parasitol, Feb. 15, 2017, vol. 235, pp. 106-112.
International Search Report and Written Opinion of the International Searching Authority for International Patent Application No. PCT/US2017/046577, dated Nov. 8, 2017, 13 pages.
International Search Report and the Written Opinion of the International Searching Authority from the Korean Intellectual Property Office in PCT/US2017/046577 dated Nov. 8, 2017.

\* cited by examiner

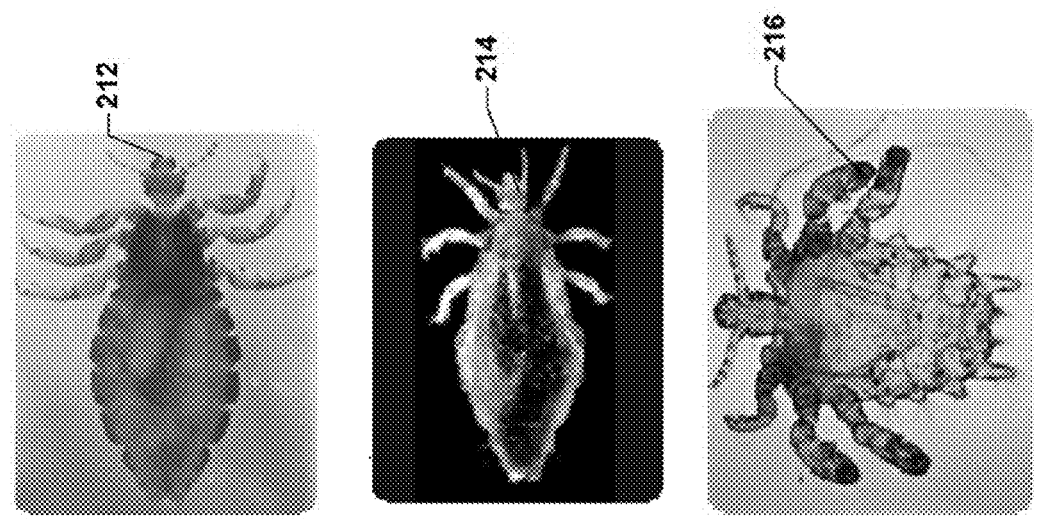
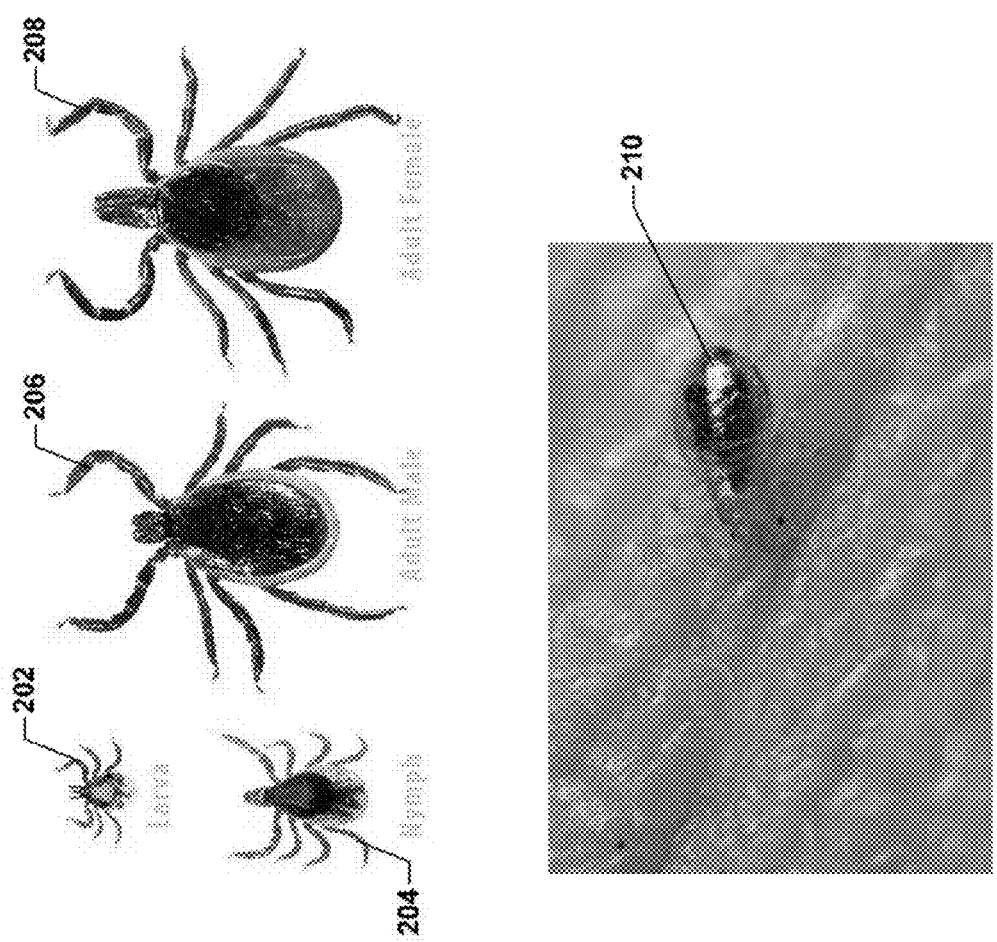
FIG. 2

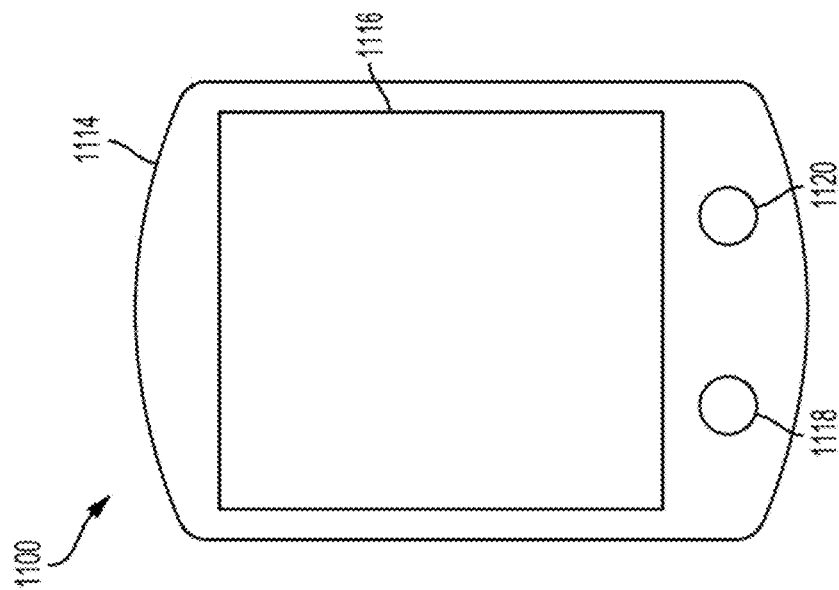
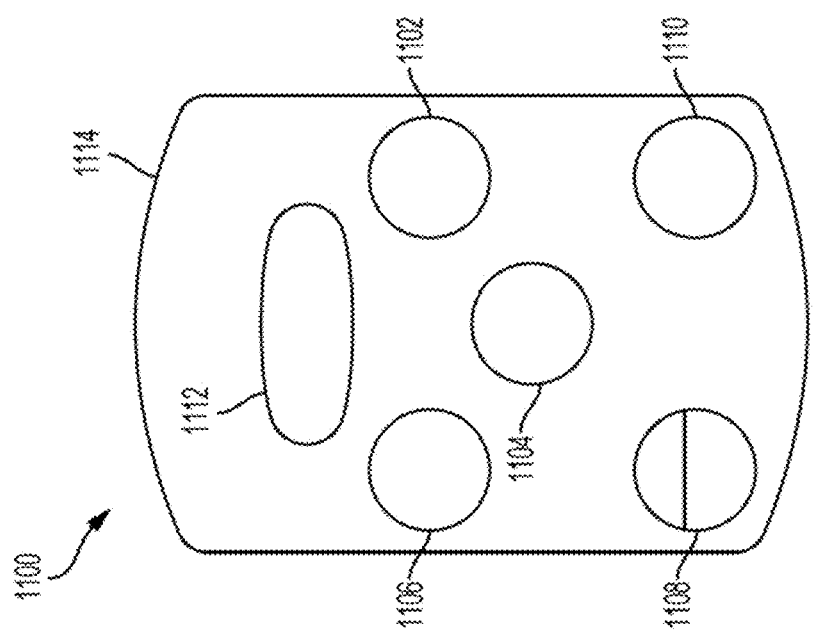

HANDHELD ARTHROPOD DETECTION DEVICE

RELATED APPLICATIONS

This application claims the benefit of priority to U.S. Provisional Application No. 62/373,578 entitled "The Handheld Arthropod Detection Wand" filed Aug. 11, 2016, the entire contents of which are hereby incorporated by reference for all purposes.

BACKGROUND OF THE INVENTION

Many arthropods are responsible for disease transmission and thus may be a major health concern. Parasitic arthropods, including arachnids such as ticks and mites and insects such as bedbugs, lice, and fleas, may be more likely to transmit disease. Early detection and removal of arthropods from a host body or various surfaces may reduce both infestation and disease transmission attributable to parasitic arthropods.

SUMMARY

Various embodiments include an arthropod detection device configured to detect, identify, and alert a user to the presence of a variety of arthropods. A method of arthropod detection using an electronic arthropod detection device may include scanning a surface or a subject using the electronic arthropod detection device, capturing, by the electronic arthropod detection device, at least one image while scanning the surface or the subject using the electronic arthropod detection device, determining whether the at least one image includes a region of interest (ROI) corresponding to an arthropod, providing an identification area of the at least one image to an object detection model in response to determining that the at least one image includes an ROI, and initiating an arthropod detected procedure in response to receiving a result from the object detection model that indicates that an arthropod is detected within the identification area of the at least one image.

In some embodiments, capturing the at least one image while scanning the surface or the subject using the electronic arthropod detect device may include capturing an IR image, and providing an identification area of the at least one image to the object detection model in response to determining that the at least one image includes the ROI may include defining the identification area within the captured IR image, and providing the defined identification area of the captured IR image to the object detection model.

In other embodiments, capturing the at least one image while scanning the surface or the subject using the electronic arthropod detect device may include capturing an IR image, and capturing an optical image, determining whether the at least one image includes a region of interest (ROI) corresponding to an arthropod may include determining whether the captured IR image includes an ROI corresponding to an arthropod, and providing an identification area of the at least one image to the object detection model in response to determining that the at least one image includes an ROI may include identifying a center point of an ROI included in the captured IR image in response to determining that the captured IR image includes an ROI, defining a search area in the captured optical image based on the center point of the ROI included in the captured IR image, defining an identification area in the captured optical image corresponding to the defined search area, and providing the defined identification area of the captured optical image to the object detection model.

In some embodiments, defining an identification area in the captured optical image corresponding to the defined search area may include scanning the search area for points of contrast, and defining the identification area in the captured optical image based on one or more identified points of contrast within the search area.

In addition, initiating the arthropod detected procedure in response to receiving the result from the object detection model may include one or more of displaying an indication that an arthropod has been detected, generating an audio indicator corresponding to the detected arthropod, displaying an image of the detected arthropod, displaying instructions associated with how to remove the arthropod from the subject or the surface, and displaying medical follow-up information.

Some embodiments may further include receiving an indication associated with a type of arthropod to be detected, and retrieving a first object detection model from a plurality of object detection models in response to receiving the indication associated the type of arthropod to be detected. The first object detection model may be used to determine whether an arthropod is detected within the identification area of the at least one image. The plurality of object detection models may correspond to one or more of a tick, a bedbug, a mite, lice, a flea, and a combination thereof.

Some embodiments may further include receiving, from a server, the object detection model, and storing the object detection model at the electronic arthropod detection device prior to providing the identification area of the at least one image to the object detection model. The object detection model may use one or more arthropod identifying characteristics to generate the result from the object detection model that indicates that an arthropod is detected within the identification area of the at least one image.

Some embodiments may further include sending at least a portion of the at least one image captured by the electronic arthropod detection device to a server. The server may update the object detection model based on the portion of the at least one image captured by the electronic arthropod detection device.

Various embodiments may include an electronic arthropod detection device. The electronic arthropod detection device may include a camera, an image sensor, a memory, and a processor coupled to the memory, the camera and the image sensor. The processor may be configured with processor-executable instructions to perform operations including capturing at least one image using the camera and image sensor while scanning a surface or a subject, determining whether the at least one image includes a region of interest (ROI) corresponding to an arthropod, providing an identification area of the at least one image to an object detection model in response to determining that the at least one image includes an ROI, and initiating an arthropod detected procedure in response to receiving a result from the object detection model that indicates that an arthropod is detected within the identification area of the at least one image. The camera and the image sensor may be included in an arthropod detection module, and the arthropod detection module may be separate from the processor.

In some embodiments, the image sensor may be a thermal image sensor configured to capture infrared (IR) images. The processor may be configured with processor-executable instructions to perform operations further comprising capturing an IR image using the thermal image sensor. The processor may be configured with processor-executable instructions to perform operations such that providing an identification area of the at least one image to the object detection model in response to determining that the at least one image includes the ROI may include defining the identification area within the captured IR image, and providing the defined identification area of the captured IR image to the object detection model.

In other embodiments, the image sensor is an optical image sensor and the electronic arthropod detection device may further include a thermal image sensor configured to capture IR images. The processor may be configured with processor-executable instructions to perform operations further including capturing an IR image using the thermal image sensor, and capturing an optical image using the optical image sensor. Determining whether the at least one image includes a region of interest (ROI) corresponding to an arthropod may include determining whether the captured IR image includes an ROI corresponding to an arthropod. The processor may be configured with processor-executable instructions to perform operations such that providing an identification area of the at least one image to the object detection model in response to determining that the at least one image includes an ROI includes identifying a center point of an ROI included in the captured IR image in response to determining that the captured IR image includes an ROI, defining a search area in the captured optical image based on the center point of the ROI included in the captured IR image, defining an identification area in the captured optical image corresponding to the defined search area, and providing the defined identification area of the captured optical image to the object detection model.

In some embodiments, the electronic arthropod detection device may further include a display, and a speaker. The processor may be configured with processor-executable instructions to perform operations such that initiating the arthropod detected procedure in response to receiving the result from the object detection model comprises one or more of displaying an indication on the display that an arthropod has been detected, communicating an audio indicator via the speaker corresponding to the detected arthropod, displaying on the display an image of the detected arthropod, displaying on the display instructions associated with how to remove the arthropod from the subject or the surface, and displaying on the display medical follow-up information.

Some embodiments may further include an input device. The processor may be configured with processor-executable instructions to perform operations further including receiving an indication associated with a type of arthropod to be detected via the input device, and retrieving a first object detection model from a plurality of object detection models in response to receiving the indication associated the type of arthropod to be detected. The first object detection model may be used to determine whether an arthropod is detected within the identification area of the at least one image. The plurality of object detection models may correspond to one or more of a tick, a bedbug, a mite, lice, a flea, and a combination thereof.

BRIEF DESCRIPTION OF THE DRAWINGS

The accompanying drawings, which are incorporated herein and constitute part of this specification, illustrate exemplary embodiments, and together with the general description given above and the detailed description given below, serve to explain the features of the various embodiments.

FIGS. 2-3 are images of exemplary arthropods that may be detected by a device according to various embodiments.

FIGS. 11A and 11B are perspective views of an arthropod detection device according to various embodiments.

DETAILED DESCRIPTION

Figure 1:
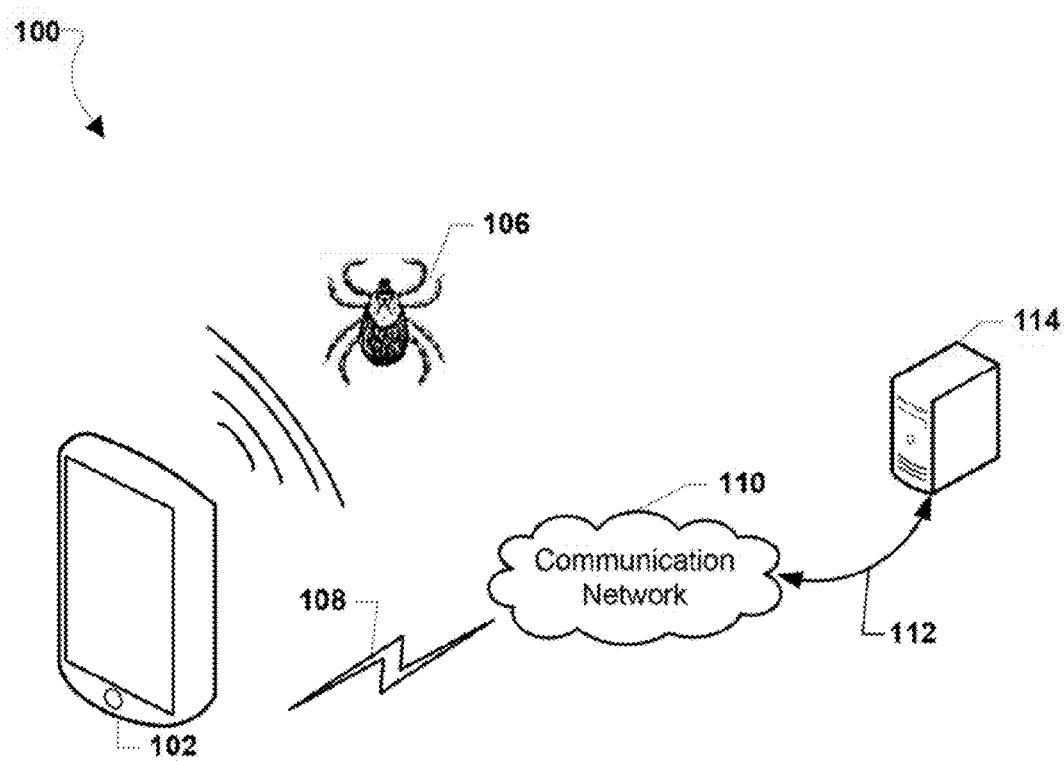
FIG. 1 is a component block diagram of a communication system suitable for use with various embodiments.

Various embodiments will be described in detail with reference to the accompanying drawings. Wherever possible, the same reference numbers will be used throughout the drawings to refer to the same or like parts. References made to particular examples and embodiments are for illustrative purposes, and are not intended to limit the scope of the various embodiments or the claims.

Various embodiments may include methods and electronic devices configured to implement methods for detecting a presence of one or more arthropods. For example, an electronic arthropod detection device may be a hand-held electronic arthropod detection device configured to be capable of scanning a surface or a subject (e.g., the skin of a human or fur of an animal), detecting and identifying arthropods, and/or alerting a user when an arthropod is detected. In various embodiments, the electronic arthropod detection device may be a standalone device, or a smartphone or another wireless device coupled to a scanning system or component.

The various embodiments may include an arthropod detection device or system configured to detect, recognize, identify, and/or alert a user to the presence of a variety of arthropods (e.g., ticks, mites, bedbugs, lice, fleas, etc.). Various embodiments may use imaging and/or acoustic detection modalities to detect an arthropod. In some embodiments, the handheld arthropod detection device may be configured with only one of the imaging modalities described herein such as high resolution digital photography along with image recognition software. In some embodiments, the handheld arthropod detection device may be configured with multiple imaging modalities in combination with image recognition software in which the user may select which imaging modality or modalities to use. In some embodiments, the handheld arthropod detection device may be configured with multiple imaging modalities and image recognition software executing on a processor that is configured to automatically select the most appropriate imaging modality or modalities to use for detecting any or a particular type of arthropod under circumstances of use. In some embodiments, the handheld arthropod detection device may include multiple imaging modalities and a processor configured with image recognition software and software configured to combine data from two or more of the imaging modalities to enhance detection of arthropods. As arthropods may be so small they are difficult to see with the unaided human eye, the arthropod detection device may use multiple imaging modalities, including high-resolution imaging sensors for the scanning and detection of the arthropods. In addition, arthropod detection device may be configured with an acoustic detection modality described herein such as one or more acoustic sound receivers in combination with signal processing software. Various embodiments of the handheld arthropod detection device may use any or all of these configurations as described in more detail below.

The arthropod detection device may include an electronic arthropod detection device that is configured to be capable of scanning a subject (e.g., a human or animal body) or a surface and alerting a user when an arthropod is detected. The arthropod detection device may be implemented as a handheld arthropod detection wand or as an arthropod detection element that can be connected to a wand or a handle to enable users to scan all surfaces of their bodies, including difficult to view areas such as the scalp, back, buttocks, and perineal area or scan another individual, animal or surface. For example, the arthropod detection device may include a handle or other attachment configured to removably couple a portion of the arthropod detection device to a smartphone or other mobile communication device. In some embodiments, the arthropod detection device may include a handle having one or more elements that allow an imaging component of the arthropod detection device to translate and/or rotate with up to six degrees of freedom. In some embodiments, the handle may include a telescoping rod and/or one or more mechanical bearings (e.g., hinges, ball bearings, etc.) to dynamically position one or more imaging components with respect to the subject or surface to be scanned for arthropods.

Using more than one type of imaging or detecting modality (e.g., IR and visible light imaging) may increase the probability that the arthropod detection device will detect an arthropod. The one or more types of imaging modalities may be used in combination with more than one type of image analysis model, which may be stored in the memory of the arthropod detection device and/or at a server that may communicate with the arthropod detection device (e.g., via the Internet and a wireless communication network). The user may be able to select one or more imaging modalities or choose the automatic mode that enables the electronic arthropod detection device to select one or more modalities as it "searches" for the presence of the arthropod(s). The one or more types of imaging analysis models for detecting arthropods within captured images may be generated by the server and the server may transmit the image analysis models to the arthropod detection device.

The imaging modalities implemented by the arthropod detection device may include one or more of the following: high resolution digital imaging, high resolution thermal imaging (e.g., an infrared (IR) camera), an ultraviolet (UV) light set at specified wavelengths to enhance the visibility of the arthropods and a high resolution UV imager.

The acoustic sound modalities implemented by the arthropod detection device may detect sounds generated by one or more arthropods. In some embodiments, the acoustic sound modalities may passively detect feeding, chewing, moving, mating, and/or warning sounds generated by the one or more arthropods. The arthropod detection device may include one or more acoustic receivers such as a microphone, a transducer, an ultrasonic detector, and a piezoelectric sensor. In further embodiments, the acoustic sound modalities may include an active mode in which ultrasound is emitted and echoes are received by the one or more acoustic receivers to determine a separation distance between the arthropod detection device and a surface being scanned (e.g., to guide a user in properly positioning the device with respect to the surface). In some instances, an active mode may be used to identify regions for closer inspection by detecting echoes from larger arthropods (e.g., large ticks hidden in fur of a pet).

Image recognition software may be employed by the arthropod detection system to "detect" the presence of the arthropod(s) through the analysis of one or more of the images (digital, thermal, UV enhanced).

When features characteristic of an arthropod species are detected by the arthropod detection device, one or more outputs of a sensor associated with each of the imaging modalities may be recorded and/or stored in the arthropod detection system. The images may automatically or selectively be recorded and stored in the arthropod detection device. The arthropod detection device may allow for the storage and transmission of images captured during scanning for record keeping and further analysis. The images may be transferable to another electronic device such as a smartphone, mobile communication device, a computer, and/or a server, which together with the arthropod detection device may function as an arthropod detection system. In addition, the arthropod detection device may generate a real-time auditory and/or visual indication to alert a user that an arthropod has been detected.

Thus, the arthropod detection device may significantly enhance detection of the presence of arthropods to allow a user to remove and/or eradicate a detected arthropod in a timely manner thus greatly reducing the risk of disease transmission, skin irritation, and/or discomfort.

Conditions where the arthropod detection device may detect arthropods otherwise difficult or impossible to see with the unaided eye may include beneath clothing, in areas obscured by hair or animal fur, arthropods too small to be readily seen, arthropods that blend in with surrounding color tones, in places with poor lighting, and in regions of the body or surfaces difficult to access and visualize. An auditory and/or visual alert may signal the user when an arthropod has been detected. Thus, the arthropod detection devices and systems of the various embodiments may allow a user to scan his or her own body, other individuals, animals, and/or various surfaces for the presence of arthropods.

The arthropod detection device may provide an effective, simple, and reliable means of detecting the presence of arthropods on a host subject and/or in the environment. The arthropod detection device may be more effective than the unaided eye at detecting these small organisms which are frequently obscured by hair and clothing.

Early and reliable detection of arthropods, many of which serve as major disease vectors, may reduce health risks posed by parasitic organisms both domestically and internationally.

The term "wireless communication device" is used herein to refer to any device that may use radio frequency (RF) communications to communicate with another device, for example, as a participant in a wireless communication network. A wireless communication device implementing various embodiments may include any one or all of mobile computing devices, laptop computers, tablet computers, cellular telephones, smartphones, personal or mobile multi-media players, personal data assistants (PDAs), smartbooks, palmtop computers, wireless electronic mail receivers, multimedia Internet enabled cellular telephones, wireless gaming systems and controllers, smart appliances including televisions, set top boxes, kitchen appliances, lights and lighting systems, smart electricity meters, air conditioning/HVAC systems, thermostats, building security systems including door and window locks, vehicular entertainment systems, vehicular diagnostic and monitoring systems, unmanned and/or semi-autonomous aerial vehicles, automobiles, sensors, machine-to-machine devices, and similar devices that include a programmable processor, memory, and/or circuitry for establishing wireless communication pathways and transmitting/receiving data via wireless communication networks. Various embodiments may be particularly useful in mobile computing and mobile communication devices, such as smart phones, tablet computers and other portable computing platforms that are easily transported to locations where rogue access points may lurk.

The terms "component," "module," "system," and the like as used herein are intended to include a computer-related entity, such as, but not limited to, hardware, firmware, a combination of hardware and software, software, or software in execution, which are configured to perform particular operations or functions. For example, a component may be, but is not limited to, a process running on a processor, a processor, an object, an executable, a thread of execution, a program, and/or a computer. By way of illustration, both an application running on a communication device and the communication device may be referred to as a component. One or more components may reside within a process and/or thread of execution and a component may be localized on one processor or core and/or distributed between two or more processors or cores. In addition, these components may execute from various non-transitory computer readable media having various instructions and/or data structures stored thereon. Components may communicate by way of local and/or remote processes, function or procedure calls, electronic signals, data packets, memory read/writes, and other known computer, processor, and/or process related communication methodologies.

Various embodiments may be implemented within a variety of communication systems 100, an example of which is illustrated in FIG. 1. The communication system 100 may include an arthropod detection device 102, communication network 110, and a server 114.

The arthropod detection device 102 may include an electronic arthropod device configured to scan, detect, identify, and/or generate an alert to indicate whether an invertebrate 106 is present on a subject or a surface. While FIG. 1 illustrates the invertebrate 106 as a tick, the invertebrate 106 may be any invertebrate such as a parasitic arthropod or insect including ticks, mites, bedbugs, lice, fleas, etc. The subject may include a human host or an animal host such as a dog, a cat, a horse, a deer, etc. The surface be any surface such as an environmental surface (e.g., a tree, a grass, a bush, a rock, etc.), a woven surface (e.g., fabric, clothing, etc.), etc. The arthropod detection device 102 may include a processor configured with processor-executable instructions to implement one or more image analysis techniques to scan, detect, and/or identify the invertebrate 106.

The arthropod detection device 102 may include one or more communication interfaces configured to allow the arthropod detection device 102 to wirelessly communicate with the communication network 110 and/or another electronic device via a communication link 108. For example, the one or more communication interfaces of the arthropod detection device 102 may implement a relatively short-range wireless communication protocol such as Wi-Fi, ZigBee, Bluetooth, or IEEE 802.11, or a long-rage wireless communication protocol such as a cellular protocol including 3GPP Long Term Evolution (LTE), Global System for Mobility (GSM), Code Division Multiple Access (CDMA), Wideband Code Division Multiple Access (WCDMA), Worldwide Interoperability for Microwave Access (WiMAX), Time Division Multiple Access (TDMA), and other mobile telephony communication technologies. Alternatively, the arthropod detection device 102 may include one or more ports configured to allow the arthropod detection device 102 to connect with the communication network 110 and/or another electronic device via a wired cable or plug. The arthropod detection device 102 also may be a stand-alone unit that does not include a communication interface.

In some embodiments, when the arthropod detection device 102 includes a smartphone or other mobile communication device, the arthropod detection device 102 may further include another communication interface to allow the smartphone to communicate with another element of the arthropod detection device 102.

The server 114 may generate one or more arthropod identification models used to identify whether an arthropod is present during detection and/or a type of arthropod when an arthropod is present. The arthropod identification models may be generated using crowd sourcing solutions, machine learning algorithms, etc. For example, the server 114 may use machine learning techniques to intelligently and efficiently identify different arthropods using a plurality of images. The server 114 may receive a plurality of images that correspond to each type of imaging technique implemented by the arthropod detection device 102.

To generate one or more arthropod identification modules using machine learning techniques, the server 114 may evaluate a plurality of images and classify each of the images based on one or more features, characteristics, and/or aspects associated with a subject of each of the images. For example, the server 114 may analyze a large number of images to train an image recognition model to determine a type of arthropod, a species, a sex, a size, a shape, a life stage, whether the arthropod is engorged or not, the extent of engorgement, a temperature signature of the arthropod, a temperature signature of a subject, etc. The server 114 may also extract information from each image to determine a date and/or time associated with when the image was captured, a geographic location of where the image was captured, etc.

In some embodiments, the server 114 may also receive sound recordings of arthropods of various species and generate a model of recognizing species or identifying locations of for image scanning based on received sounds. For example, the server 114 may analyze a large number of sound recordings in conjunction with images to train a sound recognition model to determine a type of arthropod, a species, a sex, a size, a shape, a life stage, etc. The server 114 may also extract information from each sound recording to determine a date and/or time associated with when the sound was captured, a geographic location of where the sound was captured, etc.

In some embodiments, the server 114 may also receive ultrasound echo data obtained from arthropod detection devices 102 using active acoustic modalities while scanning arthropods of various species and generate a model for determining locations of interest for image scanning based on received ultrasound echoes.

The server 114 may generate one or more arthropod identification models. For example, the server 114 may generate an arthropod identification model for each type of arthropod that may be detected using the arthropod detection device 102. The server 114 may also generate an arthropod identification model that includes a plurality of different types of arthropods to allow the arthropod detection device 102 to identify more than one type of arthropod at a time. Each of the arthropod identification models may be based on a plurality of images, a plurality of sounds, or a combination thereof.

The arthropod detection device 102 may be in communication with the server 114 via the communication network 110. For example, the server 114 may transmit one or more arthropod detection models to the arthropod detection device 102 over communication link 112. In addition, the arthropod detection device 102 may transmit one or more images captured at the arthropod detection device 102 to the server 114 using the communication link 108. The server 114 may collect images of arthropods provided by a large number of arthropod detection devices 102, to generate a "crowd-sourced" database, and use such collected images to further refine arthropod detection models that may be sent back to arthropod detection devices 102 in periodic updates. Such updates may be via "over-the-air" updates communicated using the communication link 108.

In some embodiments, the arthropod detection device 102 may transmit images detected at the arthropod detection device 102 over the communication network 110 to a device associated with an arthropod specialist and/or a physician (not illustrated). In some embodiments, the arthropod specialist may identify characteristics in the images received from the arthropod detection device 102 and/or classify the images according to the identified characteristics. The identified characteristics and/or classifications may be used to update the object detection model. In another embodiment, the arthropod specialist and/or the physician may use the images received from the arthropod detection device 102 to further classify the arthropod, determine whether the arthropod may be a potential vector for disease, identify a potential disease associated with the arthropod, and/or assess risk of disease transmission attributable to the arthropod. For example, the images may be captured by the arthropod detection device 102. The arthropod detection device 102 may send the images to the physician and/or the arthropod specialist. The physician may review the images for diagnosis purposes (e.g., to confirm exposure to a potentially disease-transmitting arthropod). Alternatively, the physician may forward the images to the arthropod specialist for the arthropod specialist to provide an opinion as to an arthropod type including species and other characteristics that would influence the risk of disease transmission. In embodiments including acoustic modalities, sounds or echo data may also be shared with the physician and/or the arthropod specialist.

Figure 3:
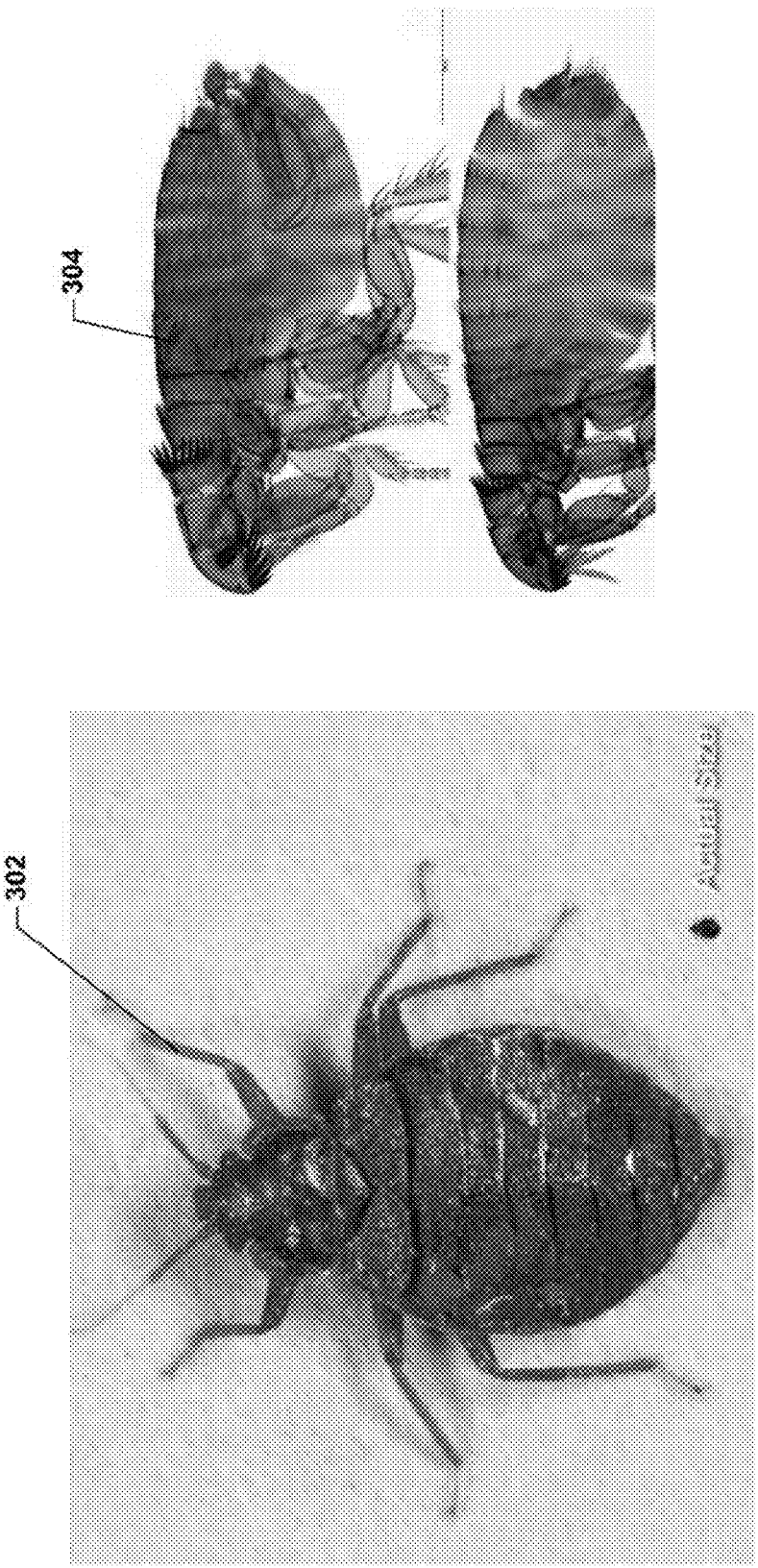

FIGS. 2-3 are images of arthropods as may be imaged by arthropod detection devices 102 and analyzed using arthropod detection models according to various embodiments. FIG. 2 includes images of ticks, a dust mite, and lice according to various embodiments. FIG. 3 includes images of a bedbug and a flea.

Arachnids such as ticks are responsible for the transmission of numerous tick-borne illnesses that can result in significant morbidity and mortality. These diseases include Lyme disease, Rocky Mountain spotted fever, Babesiosis, Ehrlichiosis, and Colorado tick fever to name a few. Tick-borne illnesses are transmitted by a variety of tick species that are identifiable by various markings and other features. The ability to identify a tick in the earliest stages of attachment to the human or animal body (ideally in <24 hours) may significantly reduce the risk of infection with Lyme disease and other tick-borne illnesses.

Cases of Lyme disease in humans have tripled over the past two decades and are now estimated to number 300,000 annually in the US alone. Lyme disease is now the most common vector-borne disease in the northern hemisphere. Undiagnosed and untreated, approximately 60% will develop chronic arthritis and 10-20% will develop debilitating neurological and cardiac disorders including dementia, peripheral neuropathies, and cardiac arrhythmias/conduction disorders. Lyme disease in pregnancy can lead to miscarriage and stillbirth. In canines, approximately 1 in 16 will test positive for Lyme disease, also leading to chronic debilitating conditions if left untreated.

Lyme disease is caused by the bacterium *Borrelia Burgdorferi*. Two species of tick are known vectors of the disease. The Blacklegged tick (deer tick or *Ixodes Scapularis*) is endemic to the northeastern, midatlantic and north-central United States. The Western Blacklegged tick (*Ixodes Pacificus*) is endemic to the Pacific coast.

As illustrated in FIG. 2, these tick species may go through four stages of development during their lifecycle: egg, larva 202, nymph 204, and adult (male 206 or female 208). Lyme and other tick-borne illness are transmitted during the nymph and adult stages. These stages are distinguishable by highly characteristic features including size, number of segmented legs, and dorsal shield markings. In some embodiments, the server 114 and/or the arthropod detection device 102 may use these characteristics as key features used in arthropod detection models to identify an invertebrate 106 within an image (e.g., a high-resolution visible light image) as a tick as well as a specific species (e.g., deer tick, etc.).

The CDC (Centers for Disease Control) has outlined strategies for reducing the risk of human exposure to Lyme disease and other tick-borne illness. These strategies include avoidance of tick habitats (grassy wooded areas), efforts to reduce tick habitats in residential areas through landscaping and keeping grass well cut, use of tick repellants on humans and dogs (application of products with 20-30% DEET to the skin and 0.5% permethrin to clothing are recommended for humans), and visual inspection for tick detection and removal.

Since it is virtually impossible to eliminate the risk of tick exposure, visual inspection of oneself and others is critical to Lyme disease and other tick-borne illness prevention. Unfortunately, ticks are often difficult to detect with the unaided eye due to multiple factors, thus increasing the risk of contracting Lyme disease. First, the majority of cases of Lyme disease are transmitted by ticks during the nymph stage when they are quite small (<2 mm) and therefore difficult to see. Secondly, ticks tend to attach to areas along the scalp, groin, and axilla where they may be obscured by hair. Also, ticks can attach themselves to the posterior neck, lower back, behind the ears, and other areas of the body often difficult if not impossible to see when inspecting oneself. In canines, visual inspection is particularly difficult due to their thick fur. Finally, ticks secrete a natural anesthetic when attaching to the host making detection even more difficult.

Aside from an individual performing a visual scan, there are currently no other methods for aiding in the detection of ticks, which have attached to their hosts. A device that can scan and immediately alert the individual to the presence of one or multiple ticks on a host is therefore desperately needed so that ticks can be located and quickly removed from the host before disease transmission.

It is desirable to also detect a presence of other arachnids such as mites. The female Sarcoptes scabiei (mite) is 0.3 to 0.45 mm long and 0.25-0.35 mm wide. Also known as the itch mite, this parasitic arthropod burrows into the skin of a human host and lays eggs, resulting in Scabies, a skin disease associated with extreme pruritus, skin irritation/ disruption and secondary bacterial skin infections. Skin rash, pustules, blisters and nodules can form as a result of allergies to the mites' eggs and feces. As illustrated in FIG. 2, a characteristic appearance of a mite 210 may include four pairs of legs, an oval shell with a flat anterior surface and convex posterior surface, covered with triangular spines. Mites can also infest domesticated dogs and cats as well as pigs and other non-domesticated mammals. Scabies is readily transmitted by contact between persons. Left untreated, scabies will progress and spread to involve new areas of the skin. Detection is critical to both effective treatment and prevention of further spread of the parasite.

By implementing different arthropod detection models (e.g., provided by a server and stored in memory), the arthropod detection device 102 of various embodiments may be configured to detect parasitic insects such as lice. Lice may have characteristic identifying features and range in size from 1.1 to 3.6 mm in length and may be transmitted through close person-to-person contact. Types include head lice 212, body lice 214, and pubic lice 216. Head and pubic lice do not transmit disease but can cause skin irritation and pruritus. Body lice (Pediculus humanus) are responsible for disease transmission including epidemic typhus (rickettsia prorazekkii), epidemic relapsing fever (Borrelia recurrentus), and trench fever (Bartonella quintana). Infections are transmitted via a louse bite or inoculation with louse feces.

Adult head lice 212 may be 2.1-3.3 mm in length. Head lice 212 may infest the head and/or neck of a host and attach eggs to the base of a hair shaft. Lice are unable to hop or fly and instead move by crawling. Adult body lice 214 may be 2.3-3.6 mm in length. Body lice 214 may live and lay eggs on clothing and only move to the skin of a host to feed. Adult pubic lice 216 may be 1.1-1.8 mm in length. Typically, pubic lice 216 may be found attached to hair in the pubic area of a host. However, sometimes pubic lice 216 may be found on coarse hair elsewhere on the body of the host such as eyebrows, eyelashes, beard, mustache, chest, armpits, etc.

By implementing different arthropod detection models (e.g., provided by a server and stored in memory), the arthropod detection device 102 of various embodiments may be configured to detect bedbugs. Bedbugs are a significant cause of pruritic skin lesions, are emerging as a potential vector for disease, and can result in significant economic hardship for families and businesses alike. As illustrated in FIG. 3, bedbugs 302 are wingless parasitic insects with 6 legs and other characteristic features making them readily identifiable. For example, bedbugs may include coloring ranges from white to brown to rusty and can measure up to 0.5 cm in size. The common bedbug (Cimex lectularius) feeds on human blood for 3 to 10 minutes before leaving its host. It then retreats to a variety of areas including bedding, mattresses, box springs, curtains, carpets, and clothing. Bites from bedbugs are initially painless but then cause itchy welts. Bedbugs are not generally believed to transmit disease. However, recent research suggests they may develop over time into a vector for Trypanosoma cruzi, a protozoan parasite responsible for Chagas disease. Currently, Chagas disease is prevalent in Mexico, Central America and South America where its main vector is the insect Triatoninae (kissing bugs). Chronic infection can lead to significant morbidity and mortality including cardiomyopathy and heart failure.

Diagnosis of the skin lesions caused by bedbugs is dependent on the specific isolation and identification of the insect. Since the parasite only spends a brief time on its host while feeding, the scanning of various surfaces, especially fabrics, is necessary to isolate and identify bedbugs. Since they can live up to a year without feeding a thorough and aggressive approach is necessary in order to eradicate the parasite. A highly effective means of screening for these parasites is essential to prevent infestation.

By implementing different arthropod detection models (e.g., provided by a server and stored in memory), the arthropod detection device 102 may be configured to detect fleas. As illustrated in FIG. 3, fleas have characteristic features including highly sclerotized bodies and measure 2-10 mm in size. Numerous varieties of fleas exist including the Ctenocephalides felis (cat flea), Ctenocephalides canis (dog flea), Tunga Penetrans (sand flea or jigger) and Pulex Irritans (human flea).

Fleas are responsible for the transmission of numerous flea-borne diseases in both humans and animals. The Plague (Y. pestis), is an example of a zoonotic disease transmitted from rodents to humans by fleas. The Plague is considered a re-emerging disease and a major international health threat. Other examples of zoonotic diseases transmissible by fleas include rickettsial infections such as murine typhus (endemic typhus, rickettsia typhus), rural epidemic typhus (rickettsia prorazekkii), and flea-borne spotted fever (Rickettsia felis). Fleas transmit these and other diseases through both the regurgitation of blood meals and through their feces to the host. Fleas can also cause significant skin irritation, rashes, and discomfort.

As with tick and mite control, bedbug, lice, and flea control strategies primarily focus on insecticides and repellants, as well as avoidance. Other than visual inspection with the unaided eye, there are no routinely employed techniques to assist in the early detection of these parasites on their hosts or on surfaces. Early detection and eradication is critical to preventing disease transmission and the development of rashes, skin irritation and discomfort in the host human and/or domestic animal.

Figure 4:
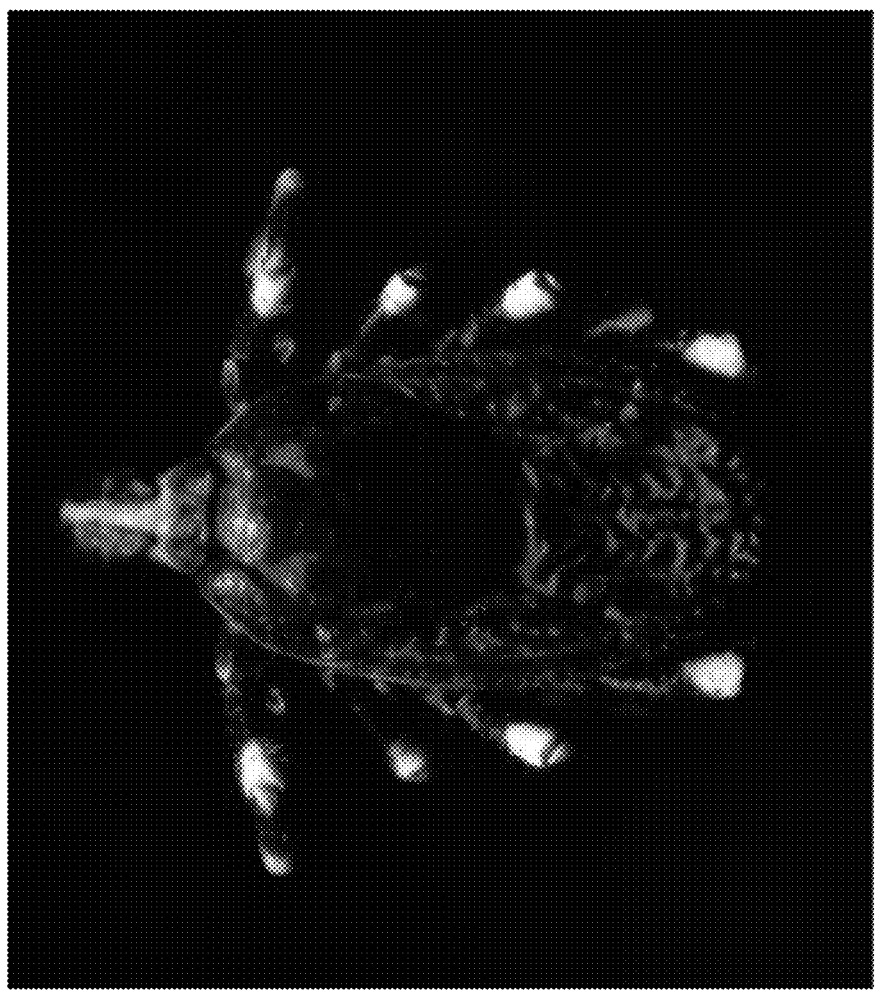
FIG. 4 is an image of a tick captured using an exemplary UVA sensor.

FIG. 4 is an image of a tick captured using an exemplary UVA sensor according to various embodiments. In addition to physical characteristics, alternative imaging techniques may be used to identify additional characteristics associated with arthropods. For example, as illustrated in FIG. 4, when a tick is exposed to light in the UVA spectrum (10 nm to 400 nm), one or more joints of the segmented legs may fluoresce at a different wavelength than the rest of the tick. In addition, the electronic arthropod detection device 502 may illuminate the subject with UV light (e.g., from a UV light source) to enhance the visibility and/or detection of other arthropods such as mites, lice, fleas, bedbugs, etc.

Figure 5:
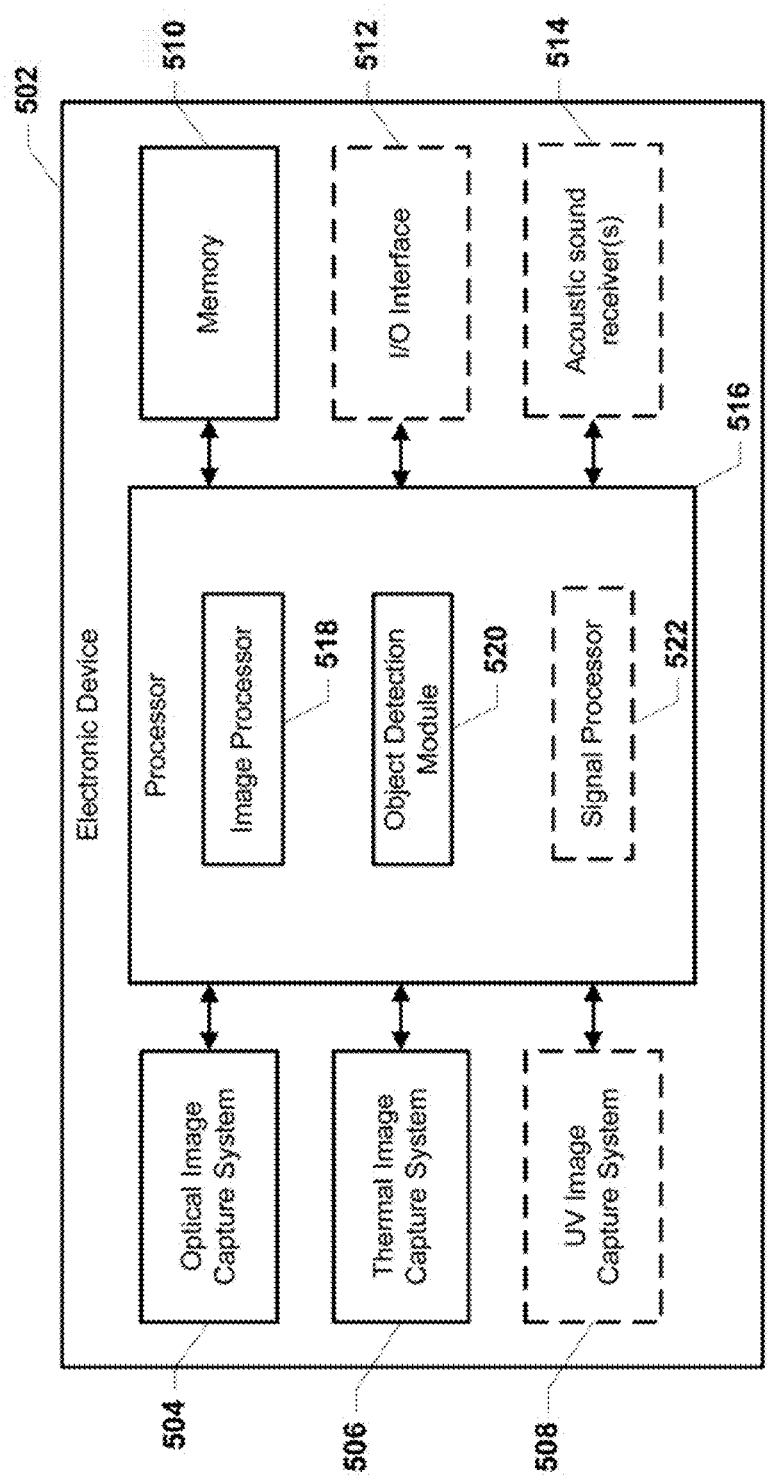
FIG. 5 is a component block diagram of an electronic arthropod detection device according to various embodiments.

FIG. 5 is a component block diagram of an electronic arthropod detection device 502 according to various embodiments. In some embodiments, the electronic arthropod detection device 502 may be the arthropod detection device 102.

The electronic arthropod detection device 502 may include an optical image capture system 504, a thermal image capture system 506, a memory 510, a processor 516, an image processor 518, and an object detection module 520. The electronic arthropod detection device 502 may optionally include an ultraviolet (UV) image capture system 508, an input/output interface 512, one or more acoustic sound receivers 514, a signal processor 522, or other sensors (not illustrated). While the image processor 518, the object detection module 520, and the signal processor 522 are illustrated in FIG. 5 as being within the processor 516, the image processor 518, the object detection module 520, and/or the signal processor 522 may alternatively be separate modules in communication with the processor 516.

The optical image capture system 504 may include one or more optical image sensors configured to capture an image of an object when the object is in the field of view of the optical image capture system 504. The thermal image capture system 506 may include one or more thermal imaging sensors configured to capture a thermal image of an object when the object is in the field of view of the thermal imaging sensor. Likewise, if the UV image capture system 508 is included in the electronic arthropod detection device 502, the UV image capture system 508 may include one or more UV image sensors.

In some embodiments, each of the optical image capture system 504, the thermal image capture system 506, and the UV image capture system 508, may include a lens assembly or camera. Alternatively, one or more of the optical image capture system 504, the thermal image capture system 506, and the UV image capture system 508 may share a lens assembly or camera The memory 510 may store instructions and/or data. For example, a camera software application may be stored in the memory 510, such that when the camera application is executed, images of one or more objects located within a field of view of the image sensors corresponding to the optical image capture system 504, the thermal image capture system 506, and the UV image capture system 508, images are captured by the corresponding image sensors. In some configurations, the images may be captured in rapid succession at a relatively high frame rate. The one or more images obtained by the electronic arthropod detection device 502 may include one or more image frames, video frame, and/or one or more still images.

In addition, the memory 510 may store images captured by the image sensors of the optical image capture system 504, the thermal image capture system 506, and/or instruction codes for performing operations by the processor 516. The memory 510 may be any electronic component capable of storing electronic information. The memory 116 may be embodied as a random access memory (RAM), read-only memory (ROM), magnetic disk storage media, optical storage media, flash memory devices in RAM, on-board memory included with the processor, EPROM memory, EEPROM memory, registers, and so forth, including combinations thereof.

The data and instructions stored in the memory 510 may include instructions executable by the processor 516 to perform one or more of the methods described herein. Executing the instructions may involve the use of the data that is stored in the memory 510. When the processor 516 executes the instructions, various portions of the instructions may be loaded onto the processor 516, and various pieces of data may be loaded onto the processor. The instructions executed by the processor 516 may include analyzing images using one or more arthropod detection models that may be store in the memory 510 or within an object detection module 520.

The processor 516 may be coupled to (e.g., in electronic communication with) the optical image capture system 504, the thermal image capture system 506, the memory 510, the ultraviolet (UV) image capture system 508, the input/output interface 512, or other sensors (not illustrated). The processor 516 may be a general-purpose single-chip or multi-chip microprocessor (e.g., an ARM), a special-purpose microprocessor (e.g., a digital signal processor (DSP)), a microcontroller, a programmable gate array, etc. The processor 516 may be referred to as a central processing unit (CPU). Although a single processor 516 is illustrated in FIG. 5, in an alternative configuration, a combination of processors (e.g., an ARM and a DSP) could be used. The processor 516 may be configured to implement the methods disclosed herein, which will be explained in detail below, to determine whether a presence of an arthropod is detected.

The image processor 518 may be configured to perform various image processing techniques on various images captured by the electronic arthropod detection device 502. In various embodiments, the image processor 518 may be configured to perform filtering, demosaicing, noise reduction, and/or image sharpening to one or more of the images captured by the electronic arthropod detection device 502. In addition, the image processor 518 may identify objects or areas or regions of interest within one or more images captured by the electronic arthropod detection device 502.

The object detection module 520 may be configured to store one or more arthropod identification models. The one or more arthropod identification models may include information associated with characteristics that may allow the electronic arthropod detection device 502 may use the one or more arthropod identification models to determine whether an arthropod is detected within an image captured by the electronic arthropod detection device 502 and/or to determine a type of arthropod detected within an image captured by the electronic arthropod detection device 502. The arthropod identification models may be generated, such as by a server (e.g., 114 of FIG. 1) using any type of images. For example, the arthropod identification models may be based on optical images, IR images, UV images, or a combination thereof. In some embodiments, if the information being sent to the object detection module 520 is from an IR image, the arthropod identification model may be generated using a plurality of IR images. Likewise, if the information being sent to the object detection module 520 is from an optical image, the arthropod identification model may be generated using a plurality of optical images.

The optional input/output (I/O) interface 512 may be configured to allow a user to interact with the electronic arthropod detection device 502 and/or receive feedback from the electronic arthropod detection device 502. The I/O interface 512 may include one or more of a user interface, an input device such as a key, button, toggle, dial, a microphone, etc., an output device such as one or more speakers and/or a motor to generate vibrations, etc., a display, a touchscreen, etc.

The one or more optional acoustic sound receivers 514 may be configured to detect a soundwave generated by an arthropod within a scan area. For example, arthropods within a scan area may generate incidental sounds such as feeding, chewing, and/or moving noises or communication sounds such as mating sounds and/or warning sounds. Incidental sounds of an arthropod may be softer and harder to detect than communication sounds.

The one or more optional acoustic sound receivers 514 may be one or more of a microphone, a transducer, an ultrasonic detector, and a piezoelectric sensor. In some embodiments, the one or more optional acoustic sound receivers 514 may further include an amplifier to amplify an electric signal generated by the microphone, the transducer, the ultrasonic detector, and/or the piezoelectric sensor to a level that is sufficient for detection.

The one or more optional acoustic sound receivers 514 may detect acoustic sound waves within the same frequency range and/or different frequency ranges. For example, a first acoustic sound receiver and/or a second acoustic sound receiver may be configured to detect soundwaves within a human audible range (e.g., 20 Hz to 20 kHz), an ultrasonic range (e.g., 20 kHz to several gigahertz), and/or a portion thereof. In some embodiments, since incidental sounds of an arthropod may be more difficult to detect than communication sounds, the first acoustic sound receiver may be tuned to detect incidental sounds of an arthropod and the second acoustic sound receiver may be tuned to detect the communication sounds of the arthropod.

The optional signal processor 522 may be in communication with the one or more acoustic sound receivers 514. The optional signal processor 522 may be configured to minimize and/or filter out undesirable noise or interference detected by the one or more optional acoustic sound receivers 514. For example, the signal processor 522 may filter out sound waves outside of a predetermined frequency value. The predetermined frequency value may be a single value or a range of frequency values. In some embodiments, the predetermined frequency value may be defined for a particular arthropod species. Alternatively, the predetermined frequency value may be defined for different stages of development and/or gender for a particular arthropod species as well as for different species. For example, the predetermined frequency value associated with a tick larva may be different from an adult tick. Alternatively, the predetermined frequency value of an adult male tick may be different from the predetermined frequency value of an adult female tick. Moreover, the predetermined frequency value of a bedbug may be different from a mite, etc.

In some embodiments, arthropod acoustic signals may be digitized and/or recorded using the signal processor 522. The acoustic signals may be identified using an auditory recognition API that uses a large arthropod sound database and classification algorithms.

The acoustic sound modalities may be configured to locate a region of interest associated with an area being scanned by the arthropod detection device. For example, one or more acoustic sound modalities may be implemented to perform an initial scan on the area of a subject or surface. The result of the one or more acoustic sound modalities may be used to perform additional imaging modalities to determine whether one or more arthropods are detected within the area being scanned.

In some embodiments, the acoustic sound modalities may be used in tandem with the imaging modalities. The acoustic sound modality may be implemented to alert a user as to an area where a search using the imaging modalities should be focused. For example, one or more acoustic sound modalities may be implemented when the arthropod detection device is scanned over a mattress in a hotel room. When an indication that there is a potential for an arthropod to be detected is generated based on the results of the acoustic sound modality, the user may then focus the arthropod detection device within an area of the mattress associated with the results of the acoustic modality such that the arthropod detection device may perform imaging using IR, optical, and/or UV enhanced imaging.

Alternatively, the acoustic sound modalities may be used alone to determine whether an arthropod is detected within the scanned area of the subject or surface.

In further embodiments, the acoustic sound modalities may include an active mode in which ultrasound is emitted (e.g., from a piezoelectric emitter/sensor element) and echoes are received by the one or more acoustic receivers 514 to determine a separation distance between the arthropod detection device and a surface being scanned (e.g., to guide a user in properly positioning the device with respect to the surface). In some instances, an active mode may be used to identify regions for closer inspection by detecting echoes from larger arthropods (e.g., large ticks hidden in fur of a pet).

Figure 6:
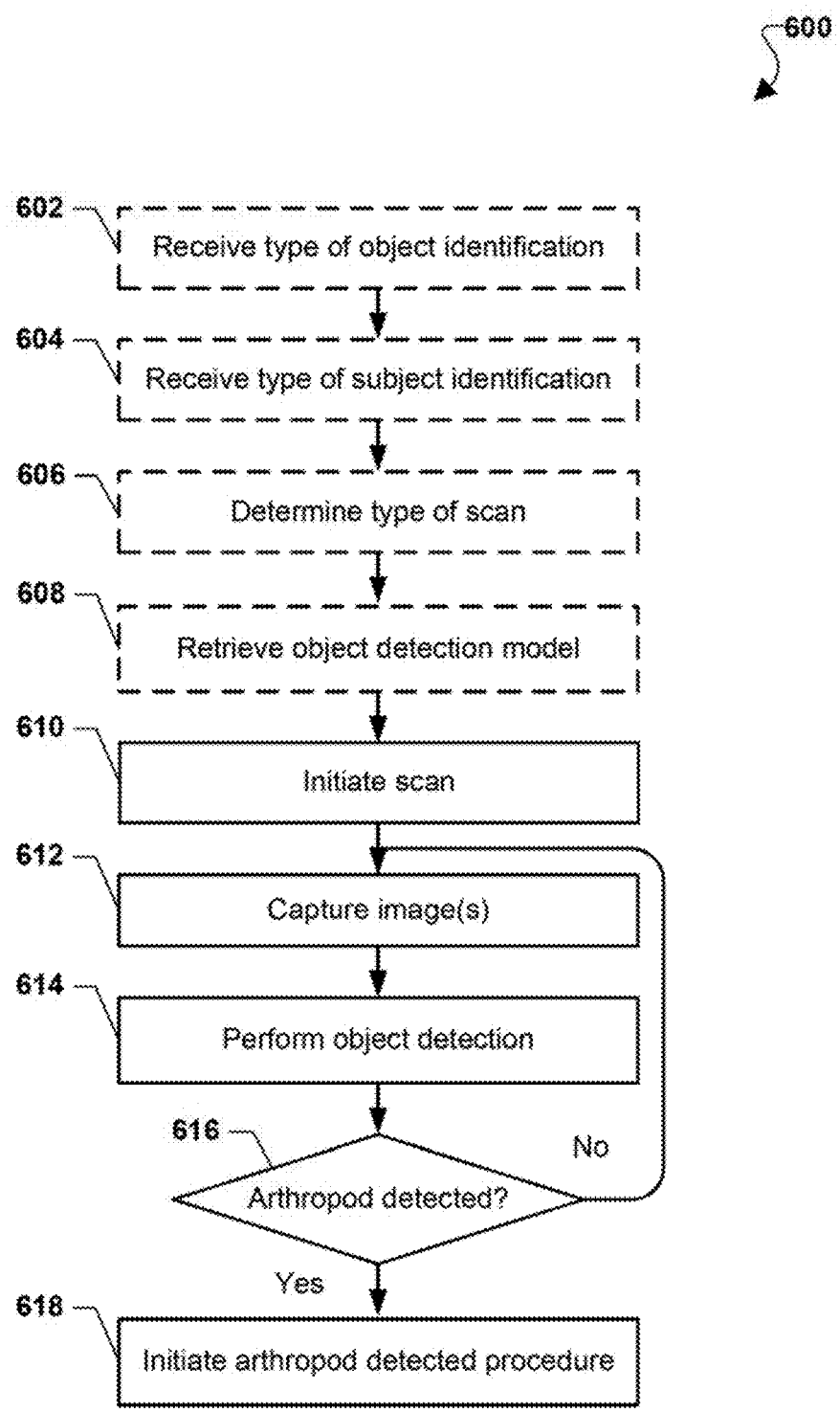
FIG. 6 is a process flow diagram illustrating a method of arthropod detection according to various embodiments.

FIG. 6 illustrates a method 600 of arthropod detection according to various embodiments. With reference to FIGS. 1 and 5, the method 600 may be implemented by one or more processors of the arthropod detection device 102 and/or the electronic arthropod detection device 502 (e.g., processor 516).

In optional block 602, the processor may receive an identification of a type of object to be detected. For example, a user may specify a particular type of arthropod to be detected during a current detection session using the I/O interface 512. If a user has been outside in the woods for a prolonged period of time, the user may select to detect for ticks. If a user wants to scan sheets or a mattress, the user may select to detect for bedbugs. Alternatively, two or more different types of arthropods may be identified to be included in the scan. In some embodiments, if no selection regarding a type of object identification is received, the processor may determine that a general scan is to be performed to initially identify a general type of arthropod and then a more detailed scan may be performed after an initial arthropod is detected.

In optional block 604, the processor may receive an identification of a type of object to be detected. For example, a user may specify whether a scan of a human subject, an animal subject, and/or a surface is desired using the I/O interface 512.

In optional block 606, the processor may determine a type of scan to be performed based on the identification of the type of object received in block 602 and/or the identification of the type of subject received in block 604. For example, a scanning procedure for a human subject may be different from a scanning procedure for an animal subject. In addition, a scanning procedure for a first type of arthropod may be different from a scanning procedure for a second type of arthropod.

In optional block 608, the processor may retrieve an object detection model based on the determined type of scan to perform. In some embodiments, the processor may retrieve a particular object detection model from the object detection module 520 from the memory 510 corresponding to the type of scan to be performed. In other embodiments, the arthropod detection device 102 may request an object detection model associated with the determined type of scan to be performed from the server 114 and the server 114 may transmit an object detection model to the arthropod detection device 102 such as the most up-to-date object detection model. Alternatively, the server 114 may periodically transmit an object detection model to the arthropod detection device 102 at predetermined time intervals.

In block 610, the processor may initiate a scan for arthropods. The scan may be initiated in various ways such as receiving an input via the I/O interface 512 of the electronic arthropod detection device 502 or detecting a predetermined gesture using the electronic arthropod detection device 502 (e.g., a scanning gesture, etc.).

In block 612, the processor may capture one or more images using the optical image capture system 504, the thermal image capture system 506, and/or the UV image capture system 508. In some embodiments, the processor may capture two or more images simultaneously using two or more different capturing systems of the electronic arthropod detection device 502. Alternatively, the processor may capture two or more images using the same capturing system of the electronic arthropod detection device 502 and/or capture two or more images using different capturing systems of the electronic arthropod detection device 502 at different times.

The images may be captured within a predetermined distance from a subject. For example, the images may be captured at about three to six inches from an inspection surface of the subject. The captured images may have various resolutions. For example, the IR camera images may be captured at a resolution of about 80×60 pixels or higher, and the visible light camera images may be captured at a resolution of about 1440×1080 pixels or higher. Increased sensitivity and accuracy of the electronic arthropod detection device 502 may be achieved by increasing the resolution of the imaging sensors. For example, the IR camera images may be captured at a resolution of about 160×120 pixels, and the visible light camera images may be captured at a resolution of about 1440×1080 pixels. In some embodiments, the IR camera images may be captured at a minimum resolution of 80×60 pixels, and the visible light camera images may be captured at a minimum resolution of 1440×1080 pixels.

In block 614, the processor may perform object detection using one or more of the images captured in block 612. For example, the image processor 518 may identify one or more regions of interest in a first captured image. A region of interest in an image may include one or more pixels that are determined to have a contrast value greater than a contrast value threshold. In some embodiments, the contrast value threshold may be a predetermined value or the contrast value threshold may be dynamically determined based on a contrast value of one or more pixels surrounding a selected pixel.

The resolution of the image sensors may influence the processing time associated with performing object detection. For example, increasing the resolution of the image sensors increases the amount of data that is processed, and thus the processing time. As processor speeds increase, the resolution of the imaging sensors may also be increased. However, increasing image resolution beyond a certain level may provide little further recognition benefits. Therefore, in some embodiments, the images captured in block 612 may be processed prior to performing object detection in block 614. For example, an additional step of resizing, rescaling, and/or resampling the one or more images captured in block 612 may be performed prior to block 614. In addition, resizing, rescaling, and/or resampling of the one or more images captured in block 612 may be performed in response to determining that a processing time associated with using the one or more images originally captured in block 612 exceeds a predetermined threshold of acceptability.

In determination block 616, the processor may determine whether an arthropod is detected. In response to determining that an arthropod is not detected (i.e., determination block 616="No"), the processor may return to block 612 and continue to capture additional images to determine whether an arthropod is detected in another portion of the scan area. In response to determining that an arthropod is detected (i.e., determination block 616="Yes"), the processor may initiate the arthropod detected procedure in block 618.

In some embodiments, the arthropod detected procedure of block 618 may include one or more of displaying an indication that a arthropod has been detected, generating an audio indicator corresponding to the detected arthropod, displaying an image of the detected arthropod, displaying instructions associated with how to remove the arthropod from the subject or surface, and displaying medical follow-up information.

Figure 7:
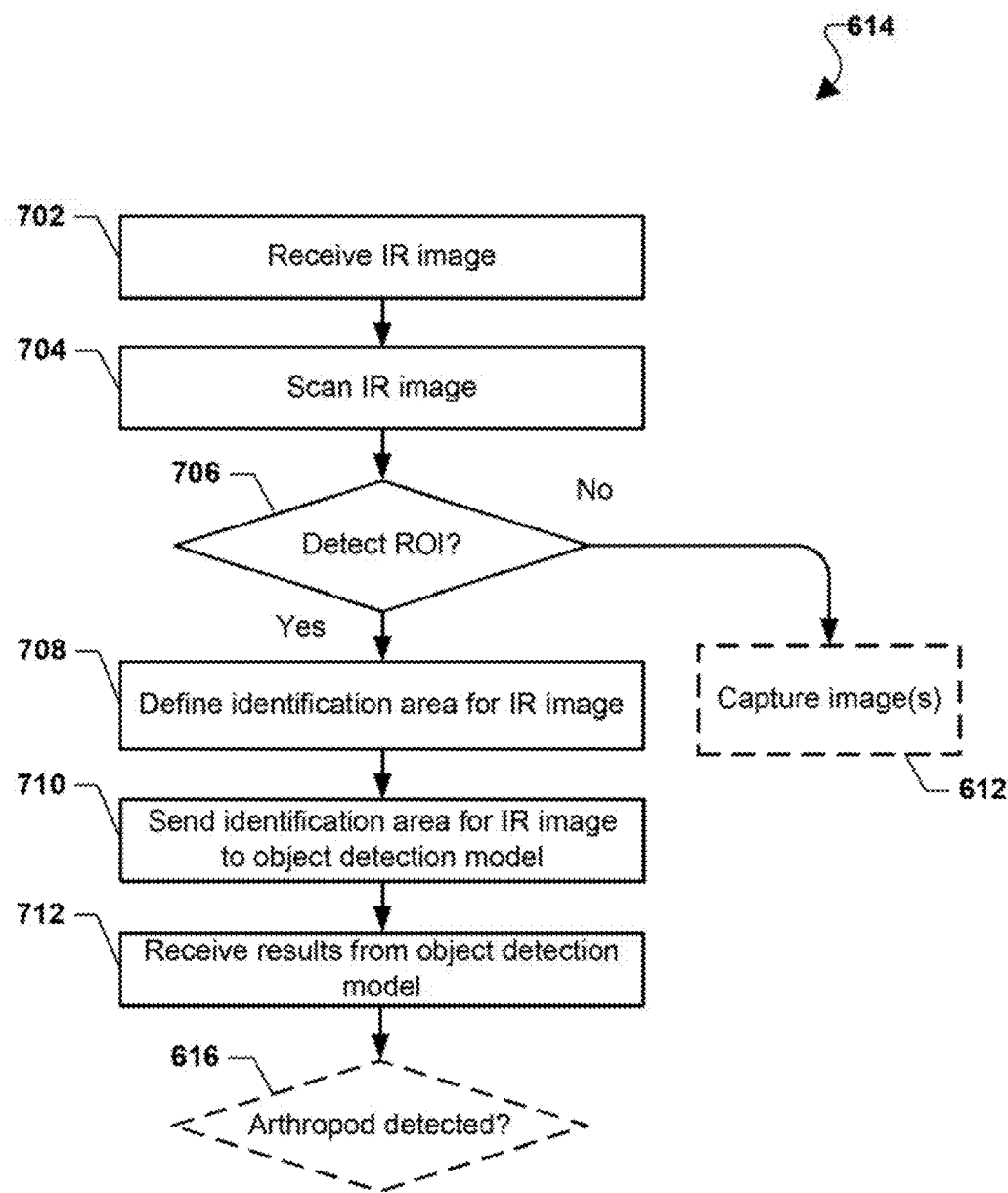
FIG. 7 is a process flow diagram illustrating a method of performing object detection according to various embodiments.

FIG. 7 illustrates an exemplary method of performing object detection 612 according to various embodiments. With reference to FIGS. 1 and 5, the method 612 may be implemented by one or more processors of the arthropod detection device 102 and/or the electronic arthropod detection device 502 (e.g., processor 516). In the method 612 illustrated in FIG. 7, operation blocks 612 and 616 may be performed as described for like numbered blocks of the method 600 illustrated in FIG. 6.

In block 702, the processor may receive one or more infrared (IR) images captured using the thermal image capture system 506. In block 704, the processor may scan the one or more IR images to determine whether each IR image includes a region of interest (ROI). For example, the processor and/or image processor 518 may scan the IR image to determine whether a pixel has a contrast value greater than a threshold contrast value.

In determination block 706, the processor may determine whether one or more ROIs are detected in the IR image. An ROI may be detected in response to determining that a plurality of pixels of a region of the IR image have a contrast value greater than the threshold contrast value. The threshold contrast value may be a single value or a ranges of values.

In some embodiments, determining whether one or more ROIs are detected in the IR image may include the processor determining whether a threshold number of pixels having a contrast value greater than the threshold contrast value are present and whether a total number of pixels corresponding to the contrast value greater than the threshold contrast value are arranged within a predetermined area or region. For example, the processor may determine that an ROI is detected in the IR image when a threshold number of pixels having a contrast value greater than the threshold contrast value are present in the IR image and the total number of pixels corresponding to the contrast value greater than the threshold contrast value are arranged in a circular region. The predetermined shape or region may correspond to each type of arthropod such that the predetermined shape associated with detecting whether a tick is present may be different from the predetermined shape associated with detecting whether a flea is present. Alternatively, the predetermined shape or region may be the same for each type of arthropod that may be detected by the arthropod detection device 102 and/or electronic arthropod detection device 502.

In response to determining that an ROI is not detected within the IR image (i.e., determination block 706="No"), the processor may return to block 612 illustrated in FIG. 6 and continue to capture additional images to determine whether an arthropod is detected in another portion of the scan area.

In response to determining that an ROI is detected (i.e., determination block 706="Yes"), the processor may define an identification area within the IR image in block 708. The defined identification area may be based on the detected ROI. For example, the processor may define the identification area to have an area greater than the detected ROI. The identification area may be defined to have any shape including a square, a circle, a rectangle, an ellipse, etc. The shape of the defined identification area may correspond to an approximate shape of the detected ROI or the shape of the defined identification may have no correlation to the shape of the detected ROI. In some embodiments, the processor may determine a center point of a detected ROI and define the identification area such that the center of the defined identification area corresponds to the center point of the detected ROI.

In block 710, the processor may send or pass the defined identification area of the IR image to an object detection module 520. For example, the processor may crop the IR image such that only the defined identification area is provided to the object detection module 520 to reduce the processing time needed to identify whether an object captured within the defined identification area and/or increase accuracy in determining whether the object includes identifying characteristics used by the object detection model.

In some embodiments, the processor may store the entire IR image and/or the defined identification area of the IR image in the memory 510. The electronic arthropod detection device 502 may use the stored IR image and/or defined identification area in future scans. Alternatively, the electronic arthropod detection device 502 may transmit the IR image and/or the defined identification area to the server 114 such that the server 114 may use the IR image and/or the defined identification area to update an object detection model.

After receiving the defined identification area of the IR image, the processor implementing the object detection model may perform various operations to determine whether one or more objects included within the defined identification area of the IR image includes identifying characteristics corresponding to the object detection model. In response to determining whether the defined identification area of the IR image includes one or more objects that have characteristics identified within the object detection model, the processor implementing the object detection model sends the results of the various operations to the processor.

In block 712, the processor may receive the results from the object detection module and then determine whether an arthropod is detected in determination block 616 of FIG. 6 based on the results. For example, the results may indicate whether or not an object within the defined identification area may be identified as an arthropod. In some embodiments, the results may include an indication of a probability that the object within the defined identification area may be an arthropod.

Figure 8:
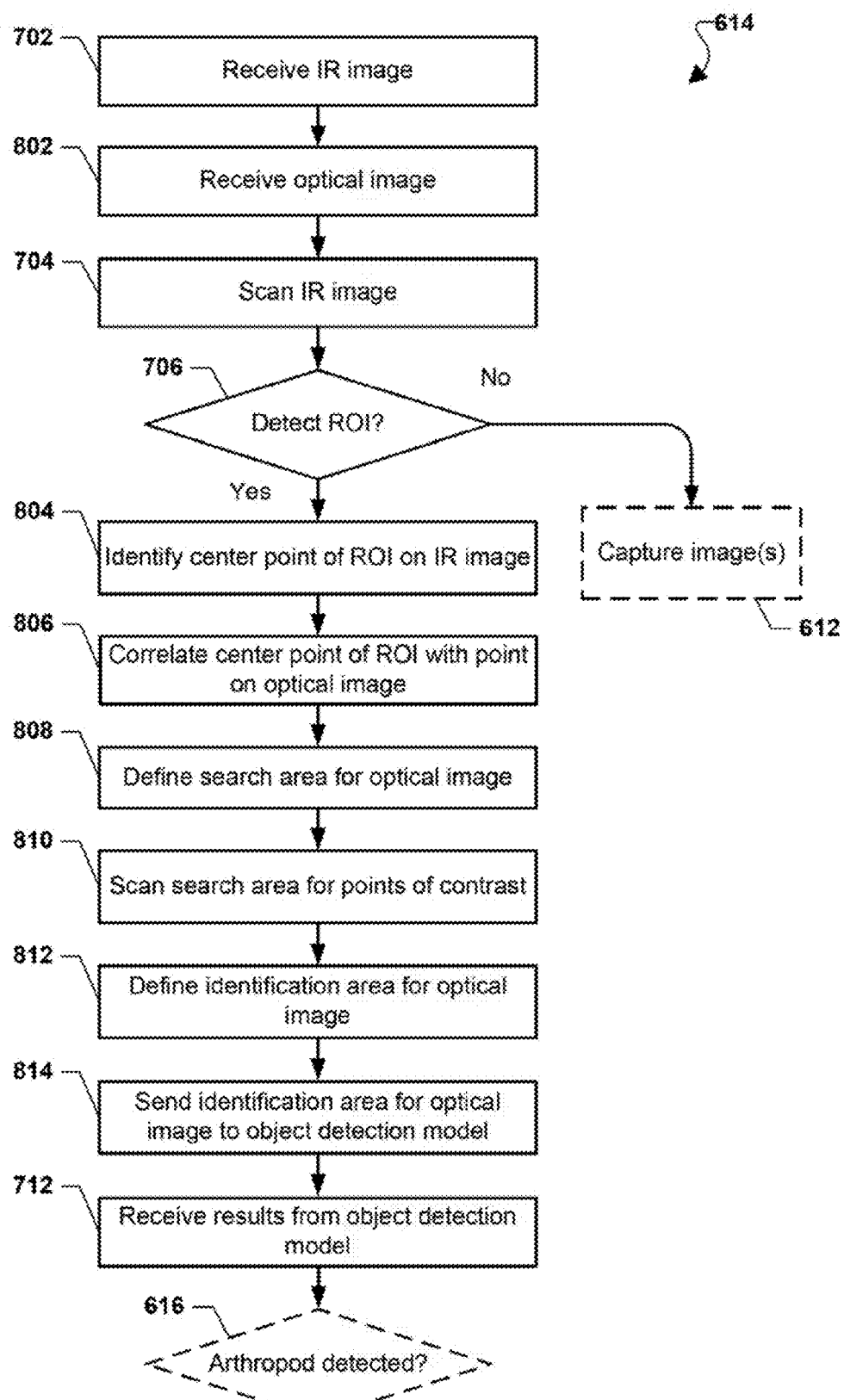
FIG. 8 is a process flow diagram illustrating another method of performing object detection according to various embodiments.

FIG. 8 illustrates another exemplary method of performing object detection 612 according to various embodiments. With reference to FIGS. 1 and 5, the method 612 may be implemented by one or more processors of the arthropod detection device 102 and/or the electronic arthropod detection device 502 (e.g., processor 516). In the method 614 illustrated in FIG. 8, operations 612, 616, 702, 704, 706, and 712 may be performed as described for like numbered blocks of method 600 illustrated in FIG. 6 and method 614 illustrated in FIG. 7.

In block 802, the processor may receive one or more optical images captured using the optical image capture system 504. While block 802 is illustrated in FIG. 8 as being performed between blocks 702 and 704, block 802 may be performed at any point during method 614. The one or more optical images may correspond to a substantially similar field of view of an area of a scan subject that is captured in the IR image. In some embodiments, one IR image may directly correlate to one optical image such that the field of view of the area of the scan subject captured in the IR image is substantially the same as the field of view of the area of the scan subject captured in the optical image. Alternatively, a plurality of IR images and/or a plurality of optical images may be processed to combine a plurality of images such that a resulting IR image and/or a resulting optical image includes a field of view of the area of the scan subject and the entire area may not have been captured in a single image.

In determination block 706, the processor may determine whether an ROI is detected within the IR image. In an exemplary embodiment, the ROI may be detected when pixels having a contrast value greater than a predetermined contrast value are arranged in a circular shape having a diameter in the range of four to 140 pixels.

In response to determining that an ROI is detected within the IR image (i.e., determination block 706="Yes"), the processor may identify a center point of the ROI in the IR image in block 804. For example, the processor may first determine an area associated with the edges of the detected ROI and then determine a center point of the area within the boundaries of the detected ROI.

In block 806, the processor may correlate the center point of the ROI detected in the IR image with a point on an optical image. The processor may identify and select an optical image that corresponds to the area of the scan subject that includes the ROI detected in the IR image. The processor may then identify a point in the optical image that is in a substantially similar location within the area of the scan subject that correlates to the center point of the ROI detected in the IR image.

In block 808, the processor may define a search area within the optical image based the ROI detected in the IR image. The search area may be arranged to cover the center point of the ROI detected in the IR image. In some embodiments, the search area may be centered with respect to the center point of the ROI detected in the IR image. The search area of the optical image may be defined to have a predetermined size and/or shape. In an exemplary embodiment, the search area of the optical image may have a square shape such that the length of each side of the square search area is twice the diameter of the ROI detected in the IR image.

In block 810, the processor may scan the search area defined within the optical image for points of contrast. In some embodiments, the processor may scan a plurality of pixels within the search area to determine whether a difference between contrast values of adjacent pixels of the optical image exceeds a predetermined threshold. The predetermined threshold may be a single value or a range of values. The processor may determine a plurality of points of contrast to identify edges of contrast.

In block 812, the processor may define an identification area within the optical image based on the results of the scan for contrasting edges within the defined search area. The processor may identify a center point of the edges of contrast identified within the defined search area and define an identification area that overlaps the center point of the edges of contrast. In some embodiments, the area of the identification area within the optical image may be substantially similar to the area of the search area defined within the optical image. Alternatively, the area of the identification area may be greater than or less than the area of the search area.

In block 814, the processor may send the identification area defined within the optical image to an object detection model. For example, the processor may send a portion of the optical image associated with the identification area defined within the optical image to the object detection module 520 where the object detection module 520 may use the object detection model to determine whether an object included in the identification area may be an arthropod.

Figure 9:
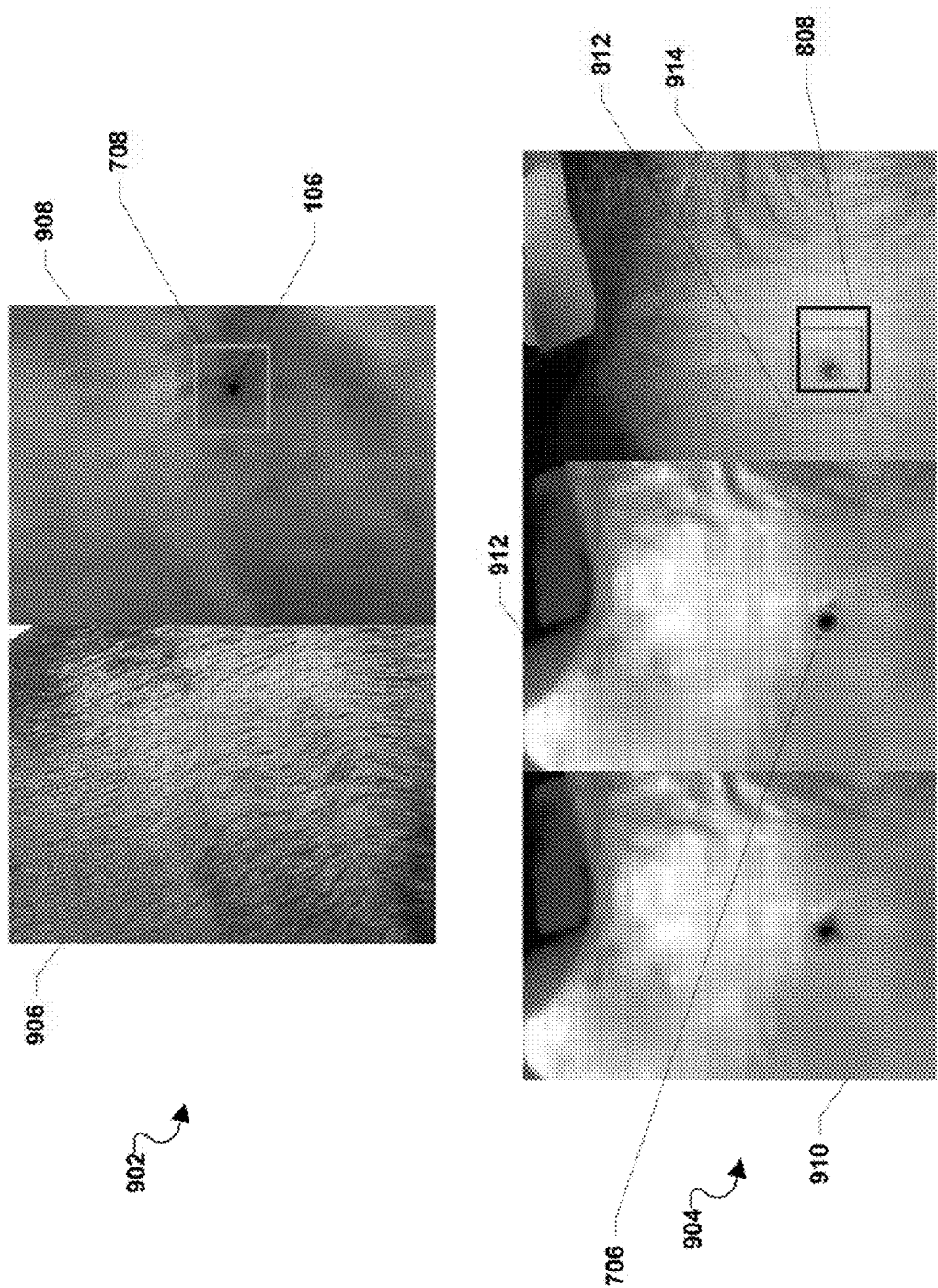
FIG. 9 are images captured during arthropod detection methods according to various embodiments.

FIG. 9 are images of a scan area for exemplary scan subjects such as animal subject 902 and human subject 904. With respect to determining whether an invertebrate 106 is present on an animal subject 902, image 908 may be an IR image of a scan area associated with the animal subject 902. Image 908 may be captured using the thermal image capture system 506 according to the methods described above. In addition, an exemplary identification area defined in block 706 is illustrated in image 908. As depicted in image 908, a heat signature of the invertebrate 106 captured in the IR image is different from the host animal subject 902 such that the IR image includes an area of high contrast that corresponds to a location of the invertebrate 106 on the animal subject. Image 906 may be an optical image of a substantially similar scan area associated with the animal subject 902. An optical image may or may not be used in a determination of whether an arthropod is detected on an animal subject. For example, consideration of whether an arthropod is present may be based solely on one or more IR images. Alternatively, one or more optical images may be used before and/or after an ROI is detected within the IR image such as in block 706 to determine whether an arthropod is present on an animal subject.

With respect to determining whether an invertebrate 106 is present on a human subject, image 910 may be captured using the thermal image capture system 506. An exemplary ROI detected in block 706 is illustrated in image 912. Image 912 may be the same image as image 910 or image 912 may be a different image from image 910. In addition, an exemplary search area defined in block 808 and an exemplary identification area defined in block 812 are illustrated in image 914.

Figure 10:
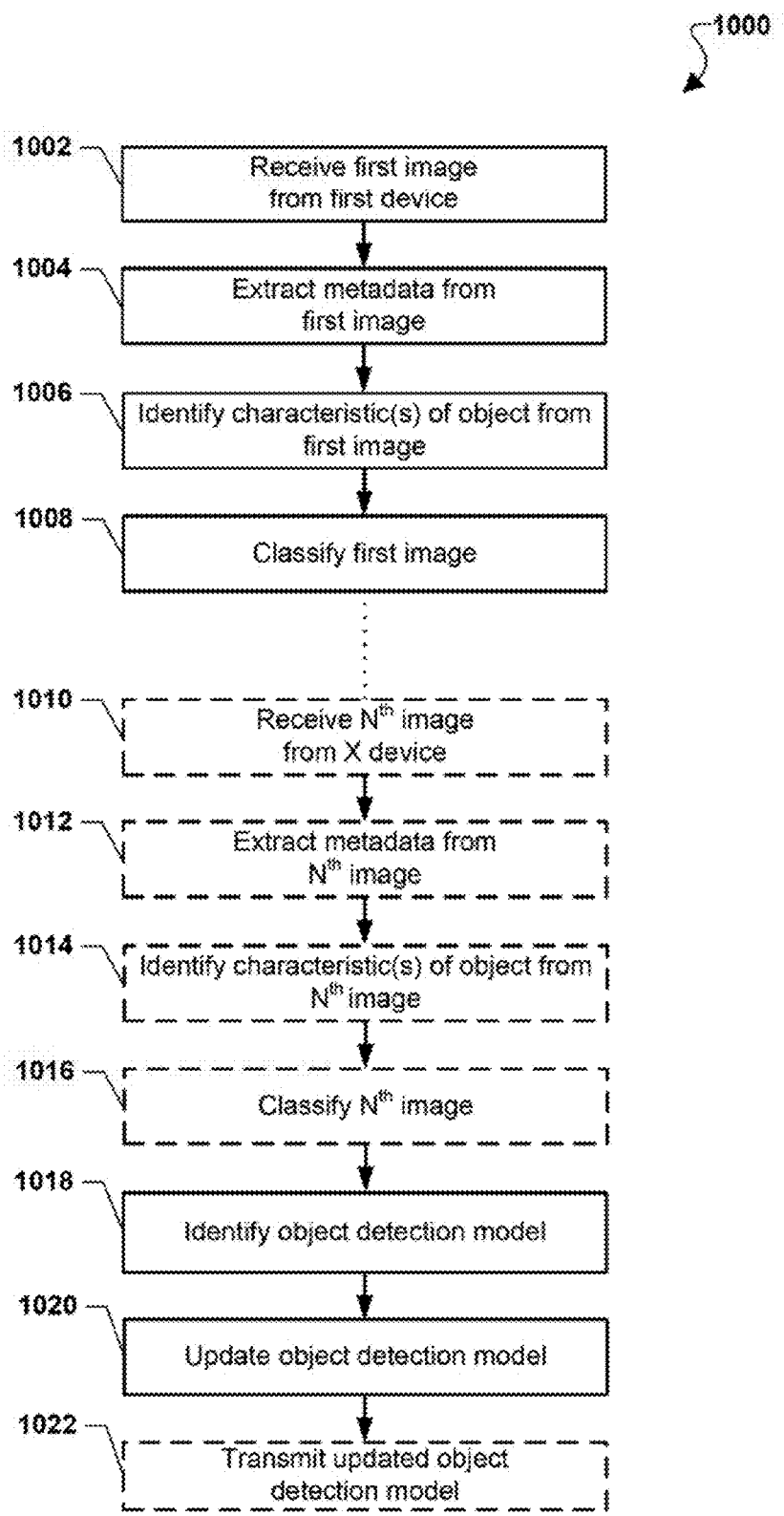
FIG. 10 is a process flow diagram illustrating a method of updating an object detection model according to various embodiments.

FIG. 10 illustrates a method 1000 of updating an object detection model according to various embodiments. With reference to FIGS. 1 and 5, the method 1000 may be implemented by one or more processors of the arthropod detection device 102, the server 114, and/or the electronic arthropod detection device 502 (e.g., processor 516). While method 1000 may be illustrated as being performed with respect to updating an object detection model, method 1000 may alternatively be performed to generate an original object detection model.

In block 1002, the processor may receive a first image from a first device. The first device may capture the first image and/or the first device may transmit the first image to the processor. In some embodiments, the first device may be the arthropod detection device 102 and/or the electronic arthropod detection device 502. The first image may be an optical image, an IR image, or a UV image.

In block 1004, the processor may extract metadata from the first image. The metadata may include information associated with one or more of a date the first image was captured, a time the first image was captured, and a geographic location in which the first optical image is captured. In some embodiments, the metadata may include a timestamp (including a date and time associated with when the image was captured) and/or GPS coordinates. The metadata may further include information associated with climate, environment, weather, etc.

In block 1006, the processor may identify one or more characteristics of an object captured in the first image. The processor may use various techniques to identify the one or more characteristics including image processing techniques, image recognition techniques, machine learning techniques, receiving user defined identifications (e.g., from an arthropod specialist or a physician), or a combination thereof. In some embodiments, the one or more characteristics may correspond to a type of invertebrate or arthropod such that an object may be identified as an arthropod when the object includes the one or more characteristics.

In block 1008, the processor may classify the first image based on the one or more characteristics of the object included in the first image. For example, if the object includes one or more characteristics that may allow the object to be determined to be a tick, the first image may be classified such that the first image may be included when an object detection model for a tick is generated.

Optionally, in block 1010, the processor may receive an $N^{th}$ image from an X device. In some embodiments, N may be any whole number and X may be any device including the first device. In optional block 1012, the processor may extract metadata from the $N^{th}$ image and in optional block 1014, the processor may identify one or more characteristics of an object included in the $N^{th}$ image. In addition, in optional block 1016, the $N^{th}$ image may be classified. Blocks 1010, 1012, 1014, and 1016 may be reiterative and may be performed any time the processor receives a new image.

In block 1018, the processor may identify an object detection model. For example, the processor may select an identifier associated with one or more of a type of arthropod (e.g., tick, bedbug, mite, lice, flea, etc.), a type of scan subject (e.g., human, animal, type of animal (e.g., dog, cat, horse, etc.), and surface), and an image format (e.g., optical, IR, etc.). The processor may retrieve a previously generated object detection model associated with the selected identifier.

In block 1020, the processor may update the identified object detection model. For example, the processor may retrieve images that have been classified to correspond with the selected identifier and then update the object detection model associated with the selected identifier to include the retrieved images that are classified to correspond with the selected identifier.

In optional block 1022, the processor may transmit the updated object detection model to one or more devices such as the arthropod detection device 102 and/or the electronic arthropod detection device 502. In some embodiments, the processor may transmit the updated object detection model in response to a request or the processor may transmit the updated object detection model at one or more discrete times including at a predetermined interval.

FIGS. 11A and 11B illustrate perspective views of an arthropod detection device 1100 according to various embodiments. FIG. 11A illustrates a front perspective view of the arthropod detection device 1100, and FIG. 11B illustrates a back perspective view of the arthropod detection device 1100.

The arthropod detection device 1100 may be a fully integrated device. For example, in some embodiments all hardware components and software components of the arthropod detection device 1100 may be provided within a single housing 1114. The arthropod detection device 1100 may include a camera 1102, a thermal (e.g., far infrared) imager 1104, the housing 1114, and a display 1116. The arthropod detection device 1100 may additionally and/or alternatively include a UV emitting lamp 1106, a first acoustic sound receiver 1108, a second acoustic sound receiver 1110, an automatic mode sensor 1112, an input device 1118, and/or an indicator device 1120. While the camera 1102, the thermal imager 1104, the UV emitting lamp 1106, the first acoustic sound receiver 1108, the second acoustic sound receiver 1110, the automatic mode sensor 1112, the display 1116, the input device 1118, and/or the indicator 1120 are illustrated in FIGS. 11A and 11B as having a certain arrangement and configuration, such components may be provided within the housing 1114 in any location, on any of the surfaces of the housing 1114 to such that elements have any arrangement and/or configuration.

The camera 1102 may be any camera including a high resolution digital camera. In some embodiments, the camera 1102 may include additional lighting capabilities such as LED auto-flash lighting to visualize arthropods. Alternatively, the arthropod detection device 1100 may further include a separate alternative flash or lighting element. The camera 1102 may capture still or video images and a user may select an imaging mode option for capturing a still image or a continuous recording mode. In some embodiments, a visual recognition API (application programming interface) may utilize a large stored arthropod image database to detect the presence of and/or identify one or more arthropods. Characteristic features such as patterning on a tick's dorsal shield, size, and/or number/positioning of legs may be used by image recognition software to classify the arthropod.

The thermal imager 1104 may be configured to capture images of arthropods not readily visual by an unaided eye such as arthropods obscured by hair, fur, clothing as well as areas with low lighting. The thermal imager 1104 may be configured to capture still or video thermograms. Thermograms may reveal a color, a size, and/or a shape of on object included in the recorded image, features of the object which may be used with image recognition software to classify the image. Arthropods may have surface temperatures that are distinct from the surrounding surface and associated with specific spectral colors as well as characteristic sizes and shapes. Thermography may allow the arthropod detection device 1100 to detect the presence of arthropods not readily visible to the unaided eye/obscured by hair, clothing or other obstructions. A visual recognition API utilizing a large database of stored arthropod thermograms (color, size, and shape) and visible light images of arthropods may be configured to detect the presence of and/or identify specific arthropods in areas that may not be visible or audible to the high-resolution digital camera and/or other imaging modalities.

The UV emitting lamp 1106 may be used to enhance the visibility of certain arthropods not readily visible by an unaided eye. Ultraviolet light at selected wavelengths may cause different arthropods to fluoresce or emit visible light with distinct colors. High definition images (still and/or video) may then be examined and compared to a large internal database of arthropod images under visible and/or ultraviolet lighting using a visual recognition API to detect the presence of and/or identify specific arthropods. A color sensor may also be used to assist in detecting the presence of arthropod fluorescence.

The arthropod detection device 1100 may include the first acoustic sound receiver 1108 and/or the second acoustic sound receiver 1110. The first acoustic sound receiver 1108 and the second acoustic sound receiver 1110 may be configured to detect active and/or passive sounds generated by one or more arthropods within a scan area. For example, arthropods within a scan area may generate incidental sounds such as feeding, chewing, and/or moving noises or communication sounds such as mating sounds and/or warning sounds. Incidental sounds of an arthropod may be softer and harder to detect than communication sounds.

The first acoustic sound receiver 1108 and the second acoustic sound receiver 1110 may be one or more of a microphone, a transducer, an ultrasonic detector, and a piezoelectric sensor. In some embodiments, the first acoustic sound receiver 1108 and/or the second acoustic sound receiver 1110 may further include an amplifier to amplify an electric signal generated by the microphone, the transducer, the ultrasonic detector, and/or the piezoelectric sensor to a level that is sufficient for detection. In some embodiments, one or both of the first acoustic sound receiver 1108 and the second acoustic sound receiver 1110 may be configured to also emit ultrasound (e.g., from a transducer or piezoelectric sensor) and to sense echoes of the ultrasound as may be returned from arthropods and/or a surface being scanned.

The first acoustic sound receiver 1108 and the second acoustic sound receiver 1110 may detect acoustic sound waves within the same frequency range and/or different frequency ranges. For example, the first acoustic sound receiver 1108 and/or the second acoustic sound receiver 1110 may be configured to detect soundwaves within a human audible range (e.g., 20 Hz to 20 kHz), an ultrasonic range (e.g., 20 kHz to several gigahertz), and/or a portion thereof. In some embodiments, since incidental sounds of an arthropod may be more difficult to detect than communication sounds, the first acoustic sound receiver 1108 may be tuned to detect incidental sounds of an arthropod and the second acoustic sound receiver 1110 may be tuned to detect the communication sounds of the arthropod.

While not illustrated, the arthropod detection device 1100 may further include a signal processor in communication with the first acoustic sound receiver 1108 and the second acoustic sound receiver 1110. The signal processor may be configured to minimize and/or filter out undesirable noise or interference detected by the first acoustic sound receiver 1108 and the second acoustic sound receiver 1110. For example, the signal processor may filter out sound waves outside of a predetermined frequency value. The predetermined frequency value may be a single value or a range of frequency values. In some embodiments, the predetermined frequency value may be defined for a particular arthropod species. Alternatively, the predetermined frequency value may be defined for different stages of development and/or gender for a particular arthropod species as well as for different species. For example, the predetermined frequency value associated with a tick larva may be different from an adult tick. Alternatively, the predetermined frequency value of an adult male tick may be different from the predetermined frequency value of an adult female tick. Moreover, the predetermined frequency value of a bedbug may be different from a mite, etc.

The automatic mode sensor 1112 may be configured to detect ambient lighting and other factors to assist the arthropod detection device 1100 in determining the most appropriate imaging modalities for detecting arthropods.

As illustrated in FIG. 11B, the arthropod detection device 1100 may further include a display 1116 configured to display information associated with a scan performed by the arthropod detection device 1100, an input device 1118 configured to receive an input (e.g., from a user), and/or an indicator device 1120 configured to provide a visual indicator of a mode, status, and/or power level of the arthropod detection device 1100.

In an exemplary embodiment, a user of the arthropod detection device 1100 may survey a region for the presence of arthropods by moving the detection device or at least an imaging sensor component over the surface while one or more of the imaging or acoustic modalities is activated and continuously recording. Alternatively, the user may use the arthropod detection device 1100 to classify an arthropod by taking one or more still images with one or more of the imaging modalities or detecting sound with an acoustic modality. In addition, a processor within the arthropod detection device 1100 may combine, compare, correlate and/or otherwise use data of two or more of a high-resolution digital camera (with or without ultraviolet lighting), an infrared thermal imaging camera, and one or more acoustic sound receivers, in order to achieve greater sensitivity and/or resolution of arthropods than achievable by any one type of sensor alone. In some embodiments, the processor may use a data fusion algorithm that correlates sensor data from two or more different types of sensors in order distinguish arthropods from background signals. For example, data from a thermal imaging camera may be used to identify portions of high-resolution images from the digital camera that should be compared to an imaging database. Any of a variety of data fusion algorithms may be implemented by the processor.

The arthropod detection device 1100 may be a standalone device configured to perform functions limited to arthropod detection or the arthropod detection device 1100 may be an electronic device capable having functionalities in addition to arthropod detection such as sending/receiving phone calls, email, SMS text, etc., recording soundwaves, playing music, capturing images, establishing communications with a communication network using one or more communication interfaces, etc. For example, the arthropod detection device 1100 may be a smartphone or other mobile communication device that leverages the one or more elements of the smartphone or mobile communication device to perform arthropod detection. Specifically, arthropod detection software may be stored in a memory and executed by one or more processors of the smartphone or mobile communication device such that the capabilities of the one or more cameras, microphone, display, speaker, etc. of the smartphone or mobile communication device are used to captured images, soundwaves, or perform processing according to the various methods described herein. For instance, the smartphone or mobile communication device may include one or more of the camera 1102, the thermal imager 1104, the UV emitting lamp 1106, the first acoustic sound receiver 1108, the second acoustic sound receiver 1110, the automatic mode sensor 1112, the display 1116, the input device 1118, and/or the indicator 1120.

In some embodiments, when a smartphone or mobile communication device is implemented as the arthropod detection device 1100 an additional attachment may be coupled to the arthropod detection device 1100 or additional image and/or sound processing operations may be implemented to enhance the capabilities of the one or more elements of the smartphone or mobile communication device leveraged for arthropod detection. For example, a filter, lens (e.g., magnification lens, etc.), IR attachment, UV attachment, or other smartphone or mobile communication camera accessory may be removably coupled to one or more cameras of the smartphone or mobile communication device to enhance the image capture capabilities of the smartphone or mobile communication device. Likewise, a microphone or other soundwave enhancement element (e.g., sonar transmitter, ultrasonic receiver, etc.) may be removably coupled to the smartphone or mobile communication device to enhance the soundwave transmission and/or detection capabilities of the smartphone or mobile communication device.

Additionally or alternatively, additional image and/or signal processing software may be stored and executed by one or more processors of the smartphone or mobile communication device to enhance images or soundwaves captured by the smartphone or mobile communication device. For example, additional image processing software may convert one type of image into another type of image (e.g., IR image to optical image or color optical image to black and white optical image, etc.) such that an ROI, identification area, and/or search area may be identified in an image generated after processing the captured image (e.g., an image not directly captured by a camera of the smartphone or mobile communication device). The smartphone or mobile communication device may alternatively transmit captured images, soundwaves, etc. via one or more communication interfaces to a server such that the server performs the processing and/or analysis.

Figure 12:
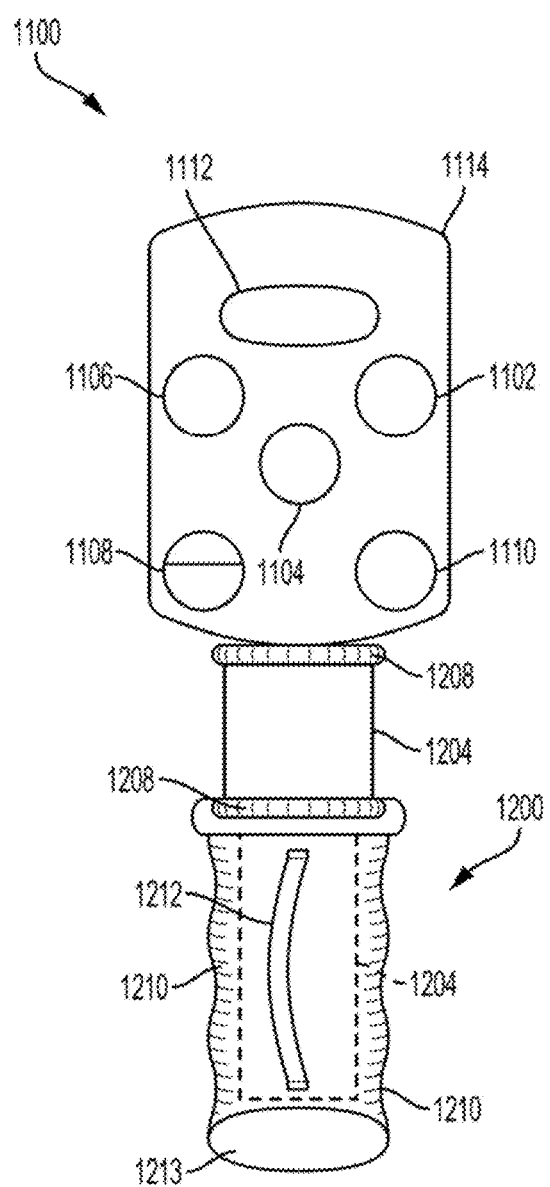
FIGS. 12 and 13 are views of another arthropod detection device according to various embodiments.
Figure 13:
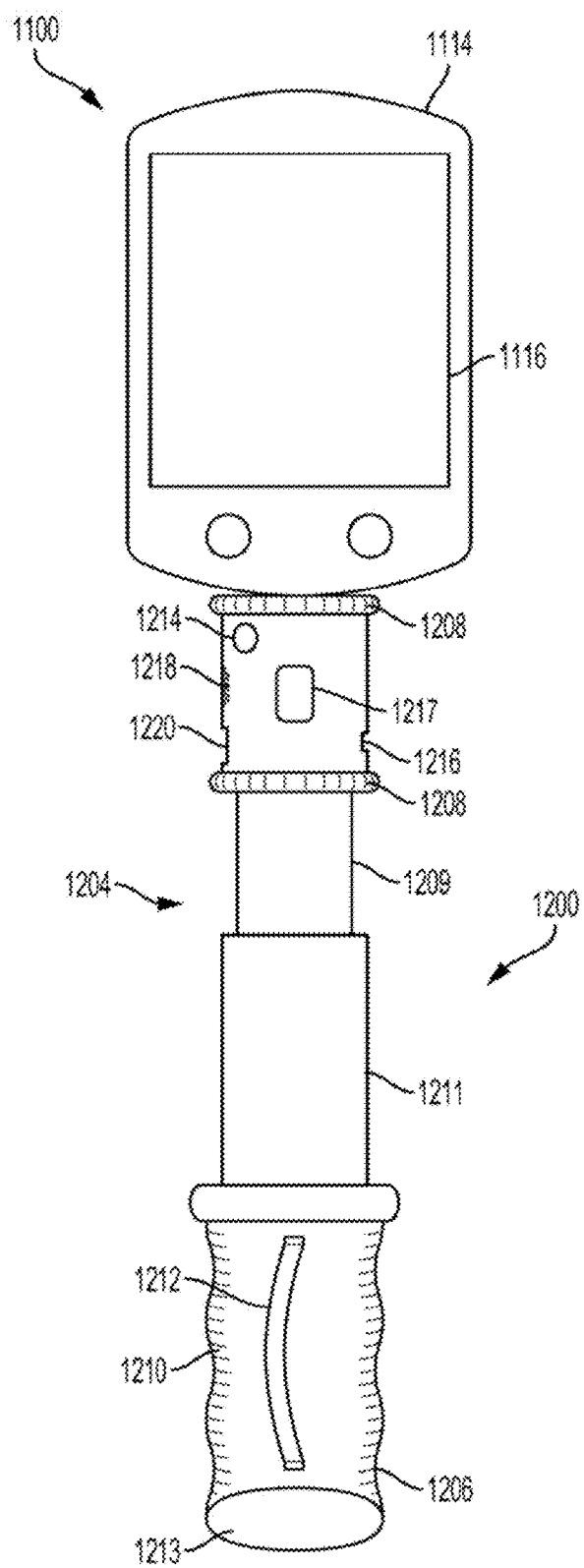
Figure 14A:
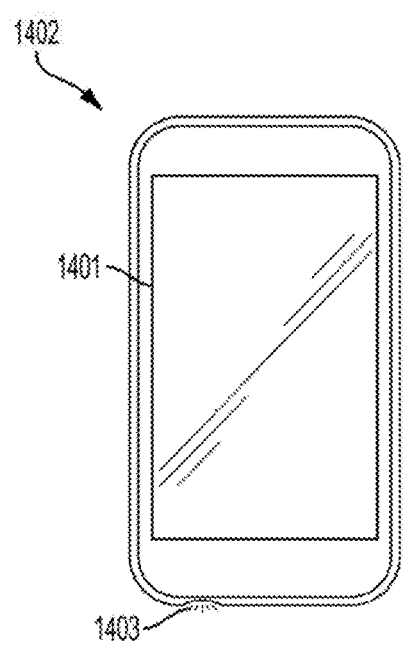
FIGS. 14A-16 are views of another arthropod detection device according to various embodiments.
Figure 14B:
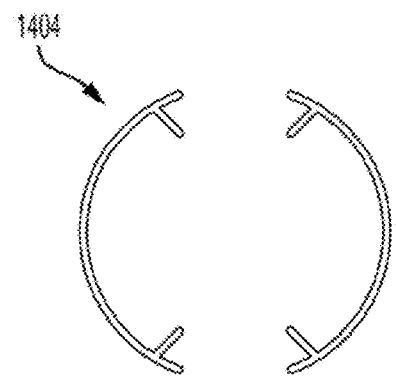
Figure 14C:
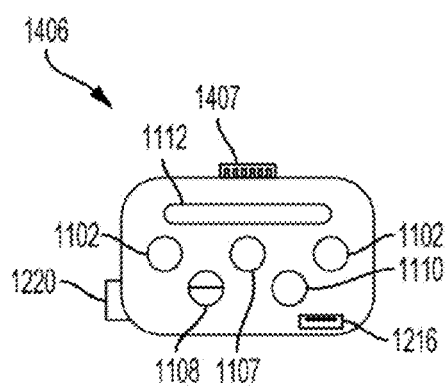
Figure 14D:
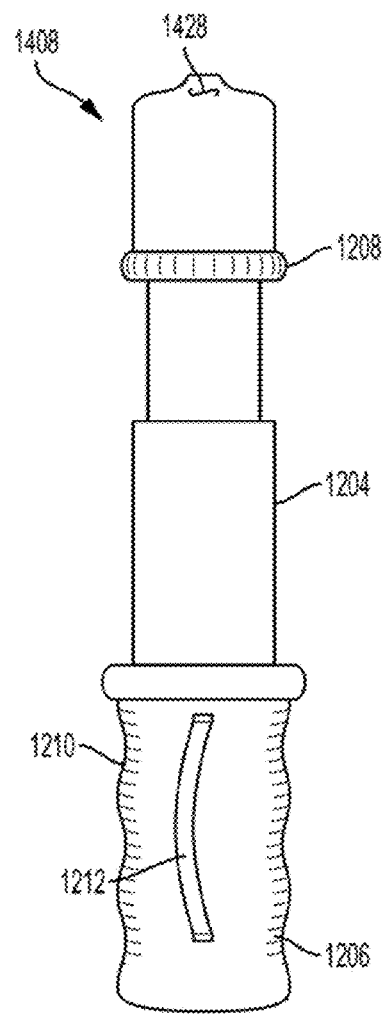

FIGS. 12 and 13 are views of the arthropod detection device 1100 coupled with a wand attachment 1200 according to various embodiments. FIG. 12 illustrates a front view of the arthropod detection device 1100 coupled with the wand attachment 1200 in which a telescoping rod 1204 of the wand attachment 1200 is retracted within a handle 1206. FIG. 13 illustrates a back view of the arthropod detection device 1100 coupled with the wand attachment 1200 in which the telescoping rod 1204 of the wand attachment 1200 is in an extended position with respect to the handle 1206.

The wand attachment 1200 may be permanently coupled to the arthropod detection device 1100 such that the telescoping rod 1204 is integrally formed with the arthropod detection device 1100. Alternatively, the wand attachment 1200 may be removably coupled to the arthropod detection device 1100 such that the wand attachment 1200 and the arthropod detection device 1100 may be selectively separated and the arthropod detection device 1100 operated without the wand attachment 1200.

The telescoping rod 1204 of the wand attachment 1202 may be configured to extend and/or retract into handle 1206 for ease in positioning of the arthropod detection device 1100 with respect to a scanning subject. The telescoping rod 1204 may allow the arthropod detection device 1100 to become more compact when the arthropod detection device 1100 is not in use. While the wand attachment 1200 is illustrated as including the telescoping rod 1204, the wand attachment 1200 may include any element that extends from the handle 1206 which is configured to allow the arthropod detection device 1100 to be positioned to scan any area of a subject or a surface.

The telescoping rod 1204 may include one or more hinges 1208 and one or more shafts 1209, 1211. While FIGS. 12 and 13 illustrate two hinges 1208 and two shafts 1209, 1211, the telescoping rod 1204 may include any number of hinges and any number of shafts 1209, 1211. The hinges 1208 may be configured and/or arranged to pivot and bend to provide flexibility such that the telescoping rod 1204 may have up to six degrees of freedom of movement for positioning the arthropod detection device 1100 in relation to a human, animal, or surface being scanned in order to optimize image results. The shafts 1209, 1211 may be configured to retract within each other such that each shaft may have a different diameter. For example, the shaft 1209 closest to the arthropod detection device 1100 may have the smallest diameter and the shaft 1211 closest to the handle 1206 may have the largest diameter.

As illustrated in FIG. 12, the handle 1206 of the wand assembly 1200 may be configured to receive the telescoping rod 1204 when the telescoping rod 1204 is in a retracted position. The handle 1206 may be configured for right or left hand use. In addition, the handle 1206 may further include a textured slip-resistant grip 1210 configured for ease and comfort of grasp as well as the ability to maintain a grasp on the handle 1206 and a dorsal strap 1212 configured to provide added protection against slippage when a scan is being performed by the arthropod detection device 1100.

In some embodiments, the wand assembly 1200 may also include a battery compartment 1213. The wand assembly 1200 may accommodate disposable or rechargeable batteries.

In addition, as illustrated in FIG. 13, the wand assembly 1200 may include a visual indicator 1214, a port 1216, an input device 1217, an output device 1218, and/or a memory card slot 1220. The port 1216 may be configured to couple the arthropod detection device 1100 and/or the wand assembly 1200 to another device. For example, the port 1216 may be configured to receive a cord to couple the wand assembly 1200 to a power source (e.g., a wall outlet) or a wired communication interface. In some embodiments, the port 1216 may be a USB port. Alternatively or additionally, the arthropod detection device 1100 and/or the wand assembly 1200 may also include a wireless communication interface (e.g., WiFi, Bluetooth, etc.) to wirelessly communicate with other devices. The wired and/or wireless interface of the wand assembly 1200 may be configured to send images or other data to another device such as a smartphone or a computer.

While FIG. 13 illustrates the port 1216, the input device 1217, the output device 1218, and/or the memory card slot 1220 arranged on a back surface of the handle 1206, the port 1216, the input device 1217, the output device 1218, and/or the memory card slot 1220 may be provided in any arrangement and/or configuration within the wand attachment 1200. For example, one or more of the port 1216, the input device 1217, the output device 1218, and/or the memory card slot 1220 may be included on a front surface of the wand attachment 1200 and/or in the handle 1206.

The input device 1217 of the wand assembly 1200 may be configured to receive a manual input (e.g., a button press or touchscreen interaction from a user). In some embodiments, in response to receiving an input at the input device 1217, a sensor and/or scanner of the arthropod detection device 1100 may be activated or deactivated, a detection modality and/or a scan mode of the arthropod detection device 1100 may be selected, and/or power to the arthropod detection device 1100 and/or the wand assembly 1200 may be turned on/off. Alternatively, the wand assembly 1200 may automatically turn the arthropod detection device 1100 and/or the wand assembly 1200 on or off when a sensor and/or a scanner of the arthropod detection device 1100 is activated or deactivated.

The display 1116 may be configured to display captured or scanned images and/or information associated with a scan performed by the arthropod detection device 1100. The display 1116 may be any type of display such as an LED display, an LCD display, an OLED display, an AMOLED display, etc. or a combination thereof. The housing 1114 may include raised, impact resistant edges 1220 configured to protect detection components of the arthropod detection device 1100 such as the camera 1102, the thermal imager 1104, the UV emitting lamp 1106, the first acoustic sound receiver 1108, the second acoustic sound receiver 1110, the automatic mode sensor 1112, the display 1116, the input device 1118, and/or the indicator 1120.

The input device 1217 may be configured to allow a user to select a specific imaging modality or multiple modalities. In some embodiments, in response to receiving an input associated with an automatic mode at the input device 1217, the arthropod detection device 1100 may automatically select one or more imaging modalities while scanning for the arthropod. The output device 1218 may be an auditory alert speaker configured to notify a user that an arthropod has been detected. The visual indicator 1214 may be configured to provide a visual indication of information associated with the arthropod detection device 1100 and/or the wand assembly 1200. For example, the visual indicator 1214 may be an LED element configured to notify a user that an arthropod has been detected and/or identified, a status and/or mode of the arthropod detection device 1100, and/or a power level of the arthropod detection device 1100 and/or the wand assembly 1200.

Figure 15:
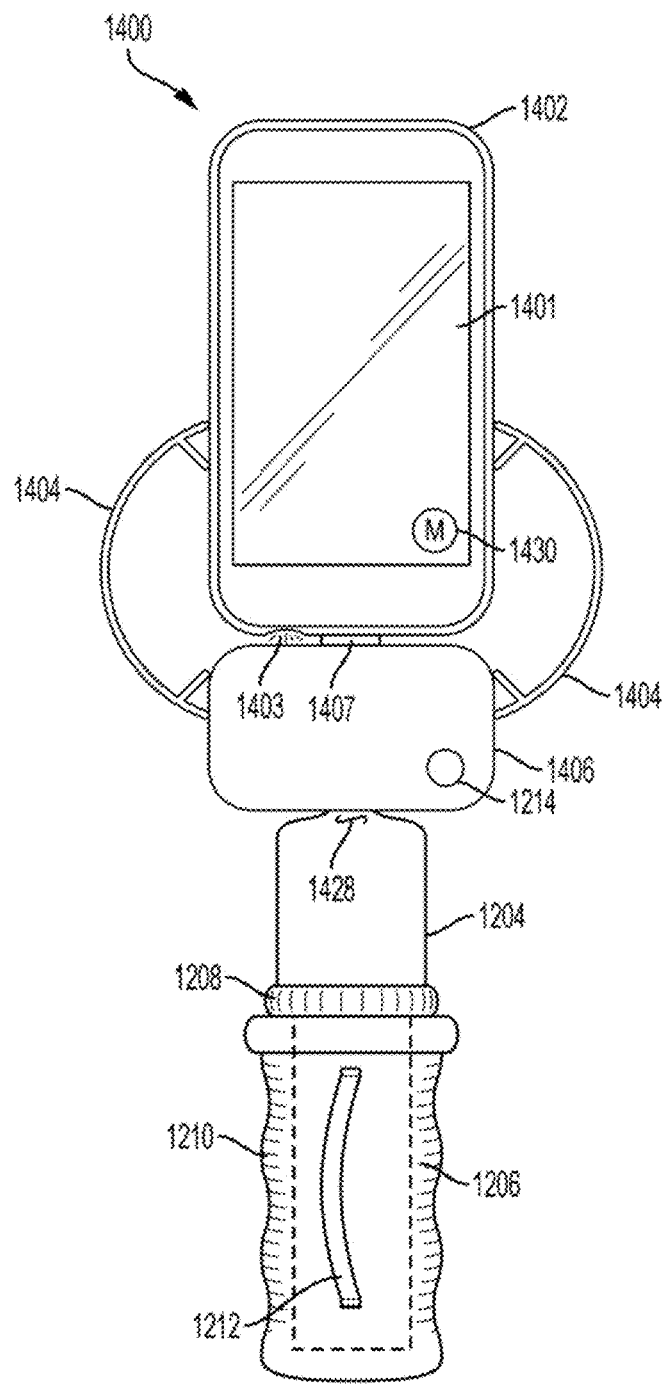
Figure 16:
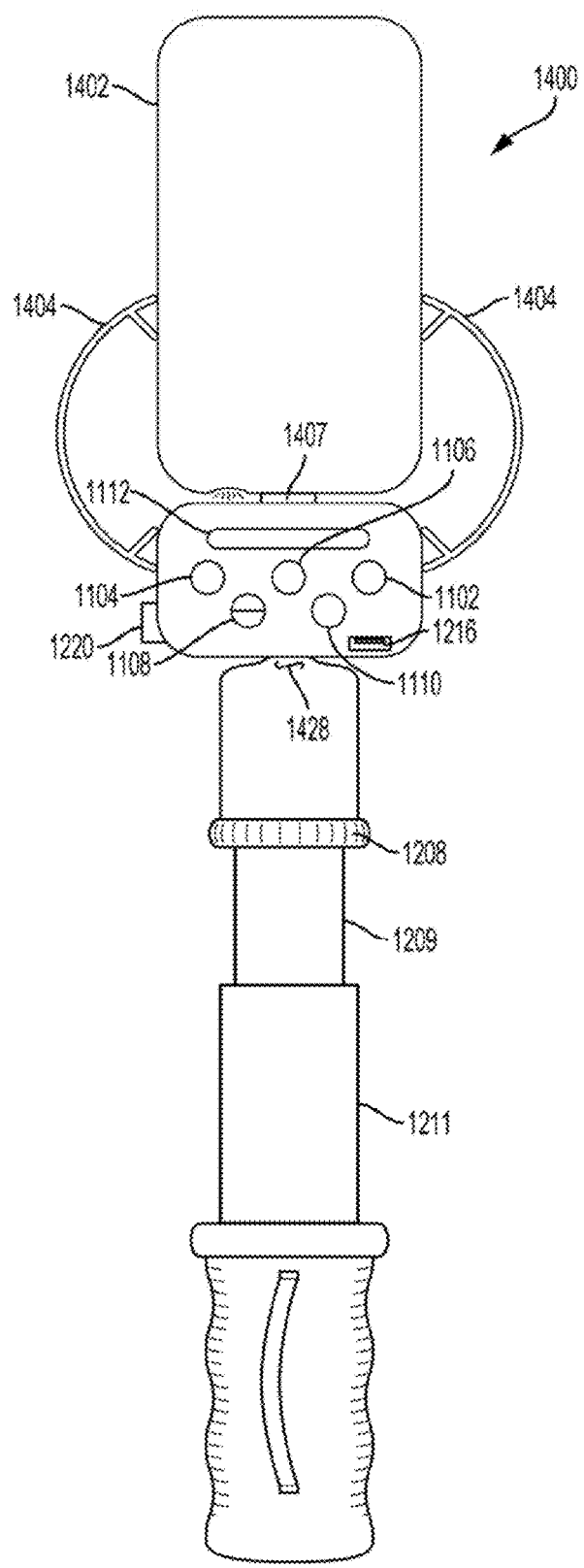

FIGS. 14-16 are views of another arthropod detection device 1400 including a processing device 1402 and an arthropod detection module 1406 according to various embodiments. FIGS. 14A, 14B, 14C, and 14D illustrates the individual components of the arthropod detection device 1400 when the arthropod detection device 1400 is disassembled. FIG. 15 illustrates a front view of the arthropod detection device 1400 when the separate components are assembled. FIG. 16 illustrates a back view of the arthropod detection device 1400 when the separate components are assembled.

As illustrated in FIGS. 14A, 14B, 14C, and 14D, 15, and 16, the arthropod detection device 1400 may include a processing device 1402, side clamps 1404, an arthropod detection module 1406, and a wand attachment 1406.

The processing device 1402 may be a wireless communication device such as a smartphone. The processing device 1402 may include a display 1401 and a speaker 1403. While not illustrated, the processing device 1402 may further include a microprocessor, application software including image and/or sound recognition software, image storage, memory, a mode selection application, and a communication interface for wireless communications.

In some embodiments, software and/or an application configured to determine whether an arthropod is detected may be stored in memory of the processing device 1402. The software and/or application may process information received from the arthropod detection module 1406 to determine whether an arthropod is detected within an area scanned by the arthropod detection device 1400. As illustrated in FIG. 15, an icon 1502 associated with the software and/or application may be displayed on the display 1401 of the processing device 1402. In response to detecting an input associated with the icon 502, the processing device 1402 may execute the software and/or application stored in the processing device 1402.

The arthropod detection device 1400 may further include side clamps 1404. The side clamps 1404 may include a first side clamp and a second side claim configured to secure the arthropod detection module 1406 to the right and left sides of the processing device 1402. While the side clamps 1404 are illustrated as having a particular size, shape, and configuration, the first side clamp and/or the second side clamp may have any shape, size, and/or configuration that allows the side clamps 1404 to secure and/or prevent the processing device 1402, the arthropod detection module 1406, and/or the wand attachment 1408 from prematurely separating after being assembled.

The arthropod detection device 1400 may include an arthropod detection module 1406. For clarity and ease of explanation, the arthropod detection module 1406 may include one or more of the like numbered components previously described with reference to FIGS. 11A and 13. Specifically, the arthropod detection module 1406 may include a camera 1102, and a thermal imager 1104, and in some embodiments, a UV emitting lamp 1106, a first acoustic sound receiver 1108, a second acoustic sound receiver 1110, an automatic mode sensor 1112, a memory card slot 1220, a visual indicator 1214, and/or a port 1216.

In addition, the arthropod detection module 1406 may further include a connector 1407 configured to allow the arthropod detection module 1406 to communicate with the processing device 1402. In some embodiments, the connector 1407 may be configured to be coupled with a port of the processing device 1402. For example, the connector 1407 may be inserted into a port of the processing device 1402 that is used to recharge the processing device 1402 or a port configured to receive an audio plug such as a headphone port. In another embodiment, the connector 1407 may be a USB connector.

The arthropod detection device 1400 may also include a wand assembly attachment 1408. For clarity and ease of explanation, the wand assembly attachment 1408 may include one or more of the like numbered components previously described with reference to FIGS. 12 and 13. Specifically, the wand assembly attachment 1408 may include a telescoping rod 1204, a handle 1206, a hinge 1208, a textured slip-resistant grip 1210, and a dorsal strap 1212.

In some embodiments, the arthropod detection module 1406 may further include a memory and/or one or more processors configured to perform one or more operations of the arthropod detection method. For example, the arthropod detection module 1406 may capture one or more images and/or soundwaves and transmit the captured images and/or soundwaves to the processing device 1402 such that the processing device 1402 performs object detection (e.g., block 614) using the captured images and/or soundwaves received from the arthropod detection module 1406. Alternatively, the arthropod detection module 1406 may perform all of the processing operations such that the arthropod detection module 1406 determines whether an arthropod has been detected (e.g., decision block 616) and sends an indication to the processing device 1402 to initiate the arthropod detected procedure (e.g., block 618).

In addition, the arthropod detection module 1406 may selectively perform one or more operations of the arthropod detection method. For example, the arthropod detection module 1406 may detect an ROI (e.g., decision block 706) and then capture additional images or send previously captured images to the processing device 1402 to define an identification area and/or a scan area. Alternatively, the arthropod detection module 1406 may detect an ROI and define an identification area and then send the results of defining the identification area to the processing device 1402.

In some embodiments, the processing device 1402 may receive information (e.g., software updates, firmware updates, an object detection model, etc.) via a communication interface of the processing device 1402 and then transfer the received information to the arthropod detection module 1406 upon being coupled via the connector 1407. Alternatively, the arthropod detection module 1406 may further include one or more communication interfaces to transmit and/or receive information from a network, the processing device 1402, or another device.

The wand assembly attachment 1408 may also include a coupling element 1428 configured to secure the telescoping rod 1204 to the arthropod detection module 1406. The coupling element 1428 may include any type of connector that allows the coupling element 1428 to be removably coupled with the arthropod detection module 1406. For example, the coupling element 1428 may be a twist and lock element, a latch, etc.

In some embodiments, the separate components of the arthropod detection device 1400 may be manually assembled by a user such that the arthropod detection device 1400 may be used to scan for and/or alert a user when arthropods are detected.

The arthropod detection devices 1100 and/or 1400 may be configured for the purpose of detecting one or more arthropods on a human, animal and/or surface, and then alerting the user if and when one or more arthropods are detected. In some embodiments, the arthropod detection devices 1100 and/or 1400 may perform similarly to a metal detector in that a user may scan a subject using the arthropod detection devices 1100 and/or 1400 at a first scan rate and in response to detecting an object that may be an arthropod, the devices 1100 and/or 1400 may emit an auditory alert. When a greater number of auditory alerts are generated, the user may scan a subject using the devices 1100 and/or 1400 at a second scan rate slower than the first scan rate. During the scans performed at the second scan rate, the devices 1100 and/or 1400 may capture additional images such as optional images received in block 802 illustrated in FIG. 8. In some embodiments, when not in use, devices 1100 and/or 1400 may be carried and stored in a full protective case designed to resist effects of impact and climate.

Figure 17:
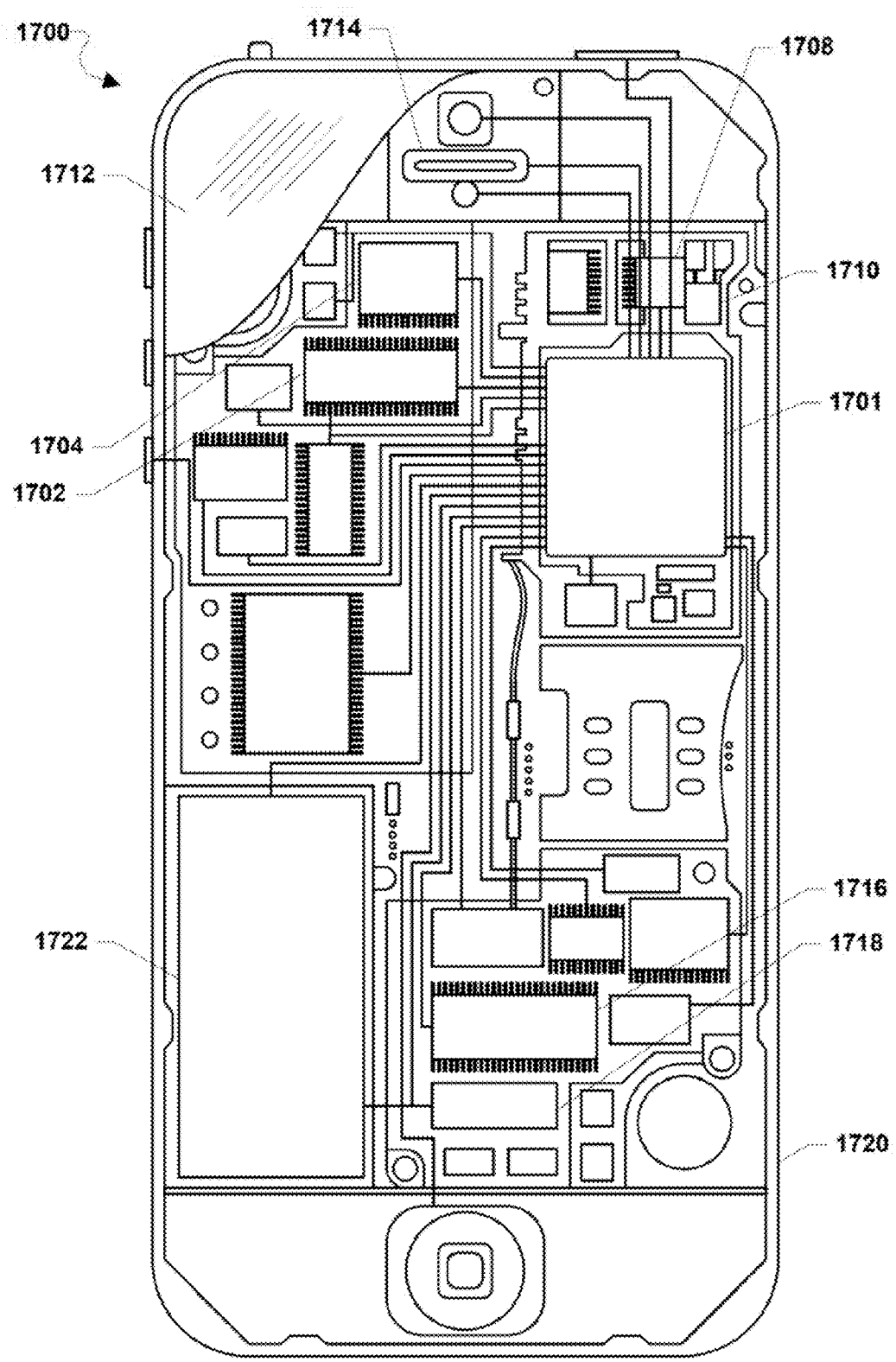
FIG. 17 is a component block diagram of a wireless communication device suitable for use with various embodiments.

The various embodiments (including, but not limited to, embodiments discussed above with reference to FIGS. 1-16) may be implemented in any of a variety of personal devices (i.e. arthropod detection device 102, electronic arthropod detection device 502, arthropod detection devices 1100 and/or 1400), an example of which is illustrated in FIG. 17. For example, the personal device 1700 may include a processor 1701 coupled to a touch screen controller 1704 and an internal memory 1702. The processor 1701 may be one or more multicore integrated circuits (ICs) designated for general or specific processing tasks. The internal memory 1702 may be volatile or non-volatile memory, and may also be secure and/or encrypted memory, or unsecure and/or unencrypted memory, or any combination thereof. The touch screen controller 1704 and the processor 1701 may also be coupled to a touch screen panel 1712, such as a resistive-sensing touch screen, capacitive-sensing touch screen, infrared sensing touch screen, etc.

In some embodiments, personal device 1700 may include one or more radio signal transceivers 1708 (e.g., Peanut®, Bluetooth®, Zigbee®, Wi-Fi, cellular, etc.) and antennae 1710, for sending and receiving, coupled to each other and/or to the processor 1701. The transceivers 1708 and antennae 1710 may be used with the above-mentioned circuitry to implement the various wireless transmission protocol stacks and interfaces. The personal device 1700 may include a cellular network wireless modem chip 1716 that enables communication via a cellular network and is coupled to the processor.

The personal device 1700 may include a peripheral device connection interface 1718 coupled to the processor 1701. The peripheral device connection interface 1718 may be singularly configured to accept one type of connection, or multiply configured to accept various types of physical and communication connections, common or proprietary, such as USB, FireWire, Thunderbolt, or PCIe. The peripheral device connection interface 1718 may also be coupled to a similarly configured peripheral device connection port (not shown).

The personal device 1700 may also include speakers 1714 for providing audio outputs. The personal device 1700 may also include a housing 1720, constructed of a plastic, metal, or a combination of materials, for containing all or some of the components discussed herein. The personal device 1700 may include a power source 1722 coupled to the processor 1701, such as a disposable or rechargeable battery. The rechargeable battery may also be coupled to the peripheral device connection port to receive a charging current from a source external to the personal device 1700.

The personal device 1700 may also include a secure area and/or a trusted execution environment. The trusted execution environment may include one or more processors and/or memory to perform secure operations that are masked from the rest of the elements of the personal device 1700. For example, the trusted execution environment may include a digital rights management (DRM) client or agent such as a content decryption module (CDM) in order to perform operations in a secure environment to reduce the risk of undesired interception of secure data.

Figure 18:
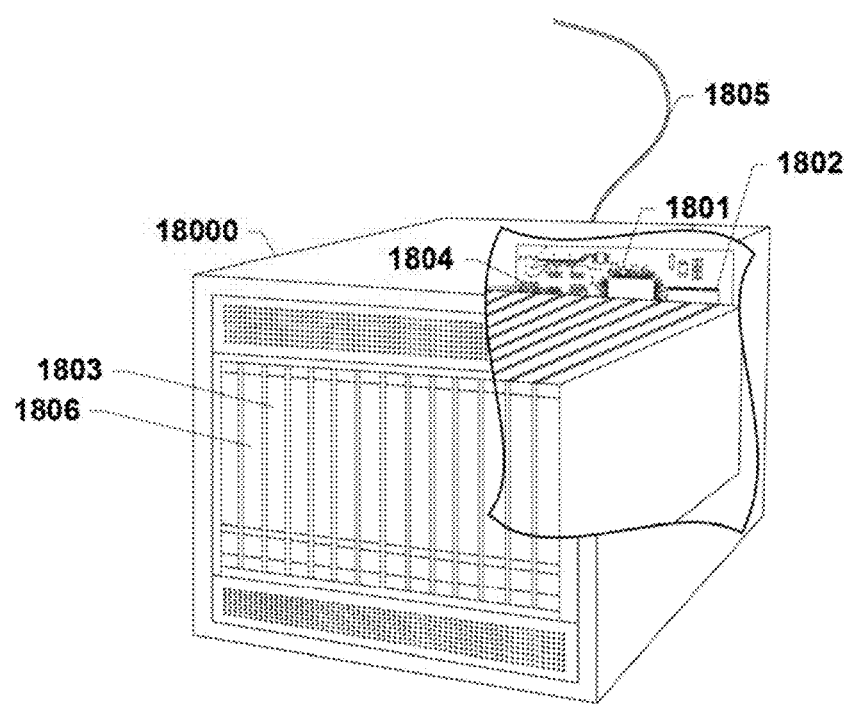
FIG. 18 is a component block diagram of a server device suitable for use with various embodiments.

Various embodiments (including, but not limited to, embodiments described with reference to FIGS. 1 and 10) may also be implemented on any of a variety of server devices, an example of which (e.g., server 114) is illustrated in FIG. 18. With reference to FIGS. 1 and 10, the server device 1800 typically includes a processor 1801 coupled to volatile memory 1802, and may also include and a large capacity nonvolatile memory, such as a disk drive 1804. The server device 1800 may also include a floppy disc drive, compact disc (CD) or DVD disc drive 1806 coupled to the processor 1801. The server device 1800 may also include network communication ports 1803 coupled to the processor 1801 for, among other things, establishing network interface connections 1807 with a communication network (such as a local area network coupled to other broadcast system computers and servers, a wide area network, a content data network, the public switched telephone network, and/or a cellular data network (e.g., CDMA, TDMA, GSM, PCS, 3G, 4G, LTE, or any other type of cellular data network). The server device 1800 may also include output ports 1808 for providing content to wireless communication devices, and/or providing content to an output device, such as a display and/or a speaker.

The processors 1701 and 1801 may be any programmable microprocessor, microcomputer or multiple processor chip or chips that can be configured by software instructions (applications) to perform a variety of functions, including the functions of the various embodiments described above. In some devices, multiple processors may be provided, such as one processor dedicated to wireless communication functions and one processor dedicated to running other applications. Typically, software applications may be stored in the internal memory before they are accessed and loaded into the processors 1701 and 1801. The processors 1701 and 1801 may include internal memory sufficient to store the application software instructions. In many devices, the internal memory may be a volatile or nonvolatile memory, such as flash memory, or a mixture of both. For the purposes of this description, a general reference to memory refers to memory accessible by the processors 1701 and 1801 including internal memory or removable memory plugged into the device and memory within the processors 1701 and 1801 themselves.

Figure 19:
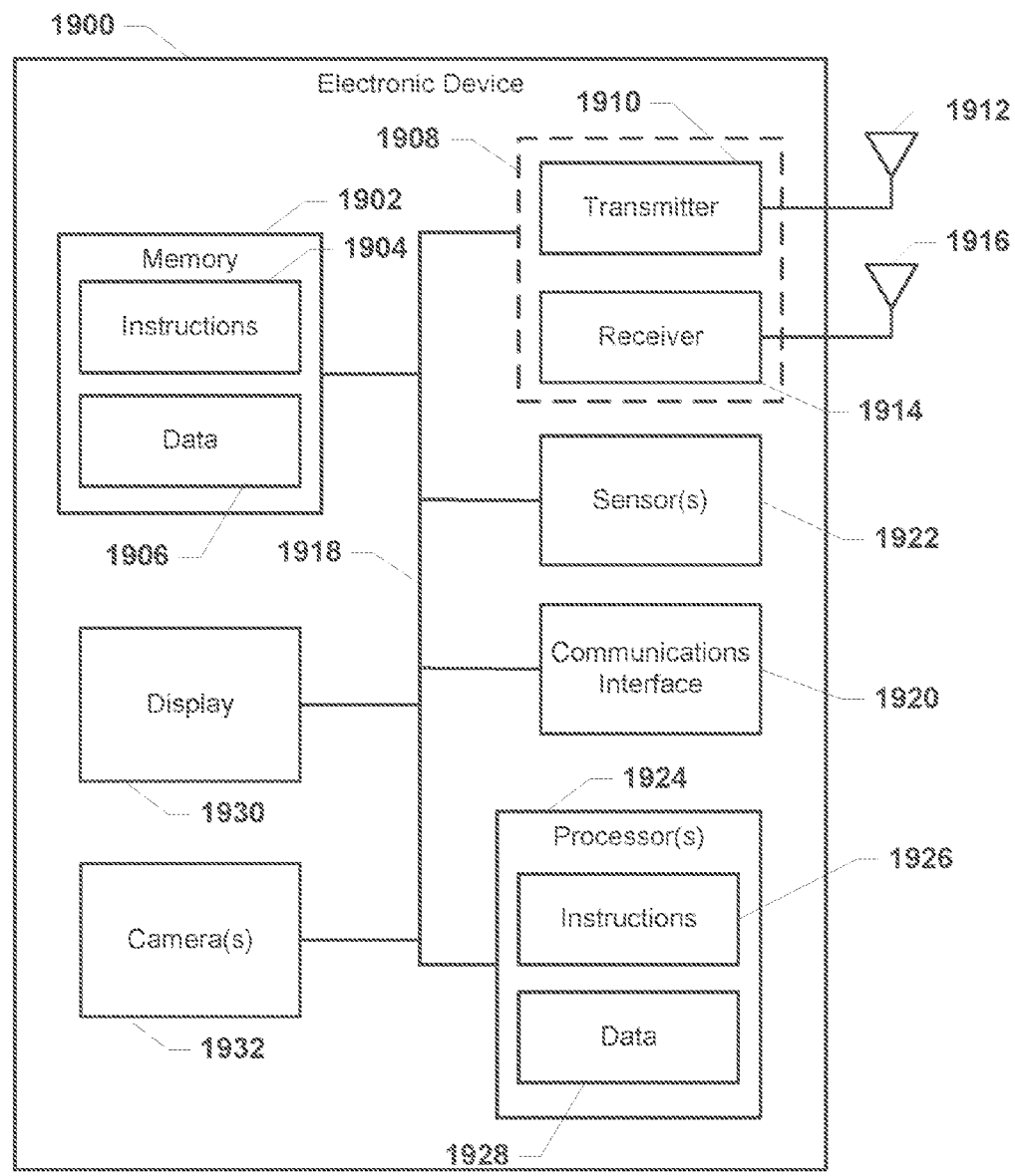
FIG. 19 is a component block diagram of another electronic arthropod detection device according to various embodiments.

FIG. 19 is a component block diagram illustrating components that may be included within an electronic device configured to implement various configurations of the systems and methods of determining whether an arthropod is present according to various embodiments. Examples of the electronic device 1900 include a camera, a video camcorder, a digital camera, a cellular phone, a smartphone, a computer (e.g., a desktop computer, a laptop computer, etc.), a tablet device, a mobile communication device, a drone, an unmanned aerial vehicle (UAV), etc. One or more of the components or elements of the electronic device 1900 may be implemented in hardware (e.g., circuitry) or a combination of hardware and software (e.g., at least one processor with instructions). The electronic device 1900 may be implemented in accordance with the arthropod detection device 102, the electronic arthropod detection device 502, and/or the arthropod detection devices 1100, 1400. The electronic device 1900 may include a processor 1924, which may be a general purpose single-chip or multi-chip microprocessor (e.g., an ARM) or a special purpose microprocessor such as digital signal processor (DSP).

The electronic device 1900 may also include memory 1902 coupled to the processor 1924. The memory 1902 may be any electronic component capable of storing electronic information. The memory 1902 may be embodied as random access memory (RAM), read-only memory (ROM), magnetic disk storage medial, optical storage media, flash memory devices in RAM, on-board memory included with the processor, EPROM memory, EEPROM memory, registers, and so forth including combinations thereof.

Data 1906 and instructions 1904 may be stored in the memory 1902. The instructions 1904 may be executable by the processor 1924 to implement one or more of the methods, procedures, operations, and/or functions described herein. Executing the instructions 1904 may involve the use of the data 1906 stored in the memory. When the processor 1924 executes the instructions 1904, various portions of the instructions 1926 may be loaded onto the processor 1924 and/or various pieces of data 1928 may be loaded onto the processor 1924.

The electronic device 1900 may also include a transmitter 1910 and a receiver 1914 to allow transmission and reception of signals to and from the electronic device 1900. The transmitter 1910 and the receiver 1914 may be collectively referred to as transceiver 1908. One or more antennas 1912, 1916 may be electrically coupled to the transceiver 1908. The electronic device 1900 may also include (not shown) multiple transmitters, multiple receivers, multiple transceivers and/or additional antennas.

The electronic device 1900 may also include a communication interface 1920. The communication interface 1920 may allow and/or enable one or more kinds of input and/or output. For example, the communication interface 1920 may include one or more ports and/or communication devices for linking other devices to the electronic device 1900. In some configurations, the communication interface 1920 may include the transmitter 1910, the receiver 1914, or both (e.g., transceiver 1908). Additional or alternatively, the communication interface 1920 may include one or more other interfaces (e.g., touchscreen, keypad, keyboard, microphone, camera, etc.). The communication interface 1920 may enable a user to interact with the electronic device 1900.

The electronic device 1900 may also include one or more sensor(s) 1922. The one or more sensor(s) 1922 may be any type of sensor including a proximity sensor, an ambient light sensor, an accelerometer, a near field communication sensor, a gyroscope, a magnetometer, a temperature sensor, a barometric pressure, a color sensor, an ultraviolet sensor, a GPS sensor, etc.

In addition, the electronic device 1900 may further include a display 1930 and one or more camera(s) 1932. The one or more camera(s) 1932 may include optical components configured to capture one or more images. In some embodiments, camera(s) 1932 of the electronic device 1900 may include two or more image sensors configured to capture images at different wavelengths. For example, the camera(s) 1932 may be configured to capture optical images, IR images, and/or UV images. The display 1930 may be configured to display information including information associated with one or more images captured by the camera(s) 1932.

The various components of the electronic device 1900 may be coupled together by one or more buses, which may include a power bus, a control signal bus, a status signal bus, a data bus, etc. For the sake of clarity, the various buses are illustrated in FIG. 19 as a bus system 1918.

The foregoing method descriptions and the process flow diagrams are provided merely as illustrative examples and are not intended to require or imply that the operations of the various embodiments must be performed in the order presented. As will be appreciated by one of skill in the art the order of operations in the foregoing embodiments may be performed in any order. Words such as "thereafter," "then," "next," etc. are not intended to limit the order of the operations; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm operations described in connection with the embodiments disclosed herein may be implemented as electronic hardware, computer software, or combinations of both. To clearly illustrate this interchangeability of hardware and software, various illustrative components, blocks, modules, circuits, and operations have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some operations or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable medium or non-transitory processor-readable medium. The operations of a method or algorithm disclosed herein may be embodied in a processor-executable software module and/or processor-executable instructions, which may reside on a non-transitory computer-readable or non-transitory processor-readable storage medium. Non-transitory server-readable, computer-readable or processor-readable storage media may be any storage media that may be accessed by a computer or a processor. By way of example but not limitation, such non-transitory server-readable, computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory server-readable, computer-readable and processor-readable media. Additionally, the operations of a method or algorithm may reside as one or any combination or set of codes and/or instructions on a non-transitory server-readable, processor-readable medium and/or computer-readable medium, which may be incorporated into a computer program product.

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the present disclosure is not intended to be limited to the embodiments shown herein but is to be accorded the widest scope consistent with the following claims and the principles and novel features disclosed herein.

What is claimed is:

1. A method of arthropod detection using an electronic arthropod detection device, the method comprising:
   receiving an indication associated with a type of arthropod to be detected;
   retrieving, by the electronic arthropod detection device, an object detection model from a plurality of object detection models in response to receiving the indication associated with the type of arthropod to be detected;
   scanning a surface or a subject using the electronic arthropod detection device;
   capturing, by the electronic arthropod detection device, at least one image while scanning the surface or the subject using the electronic arthropod detection device;
   determining whether the at least one image includes a region of interest (ROI) corresponding to an arthropod;

providing an identification area of the at least one image to the object detection model in response to determining that the at least one image includes an ROI;

determining, by the electronic arthropod detection device using the object detection model, whether an arthropod is detected within the identification area of the at least one image; and initiating an arthropod detected procedure in response to determining using the object detection model that an arthropod is detected within the identification area of the at least one image.

2. The method of claim 1,
wherein capturing the at least one image while scanning the surface or the subject using the electronic arthropod detect device comprises:
  capturing an IR image; and
wherein providing an identification area of the at least one image to the object detection model in response to determining that the at least one image includes the ROI comprises:
  defining the identification area within the captured IR image; and
  providing the defined identification area of the captured IR image to the object detection model.

3. The method of claim 1,
wherein capturing the at least one image while scanning the surface or the subject using the electronic arthropod detect device comprises:
  capturing an IR image; and
  capturing an optical image;
wherein determining, by the electronic arthropod detection device using the object detection model, whether the at least one image includes the ROI comprises:
  determining whether the captured IR image includes an ROI corresponding to an arthropod;
wherein providing an identification area of the at least one image to the object detection model in response to determining that the at least one image includes an ROI comprises:
  identifying a center point of an ROI included in the captured IR image in response to determining that the captured IR image includes an ROI;
  defining a search area in the captured optical image based on the center point of the ROI included in the captured IR image;
  defining an identification area in the captured optical image corresponding to the defined search area; and
  providing the defined identification area of the captured optical image to the object detection model.

4. The method of claim 3, wherein defining an identification area in the captured optical image corresponding to the defined search area comprises:
  scanning the search area for points of contrast; and
  defining the identification area in the captured optical image based on one or more identified points of contrast within the search area.

5. The method of claim 1, wherein initiating the arthropod detected procedure in response to receiving the result from the object detection model comprises one or more of displaying an indication that an arthropod has been detected, generating an audio indicator corresponding to the detected arthropod, displaying an image of the detected arthropod, displaying instructions associated with how to remove the arthropod from the subject or the surface, and displaying medical follow-up information.

6. The method of claim 1, wherein the plurality of object detection models correspond to one or more of a tick, a bedbug, a mite, lice, a flea, and a combination thereof.

7. The method of claim 1, further comprising:
  storing the object detection model at the electronic arthropod detection device prior to providing the identification area of the at least one image to the object detection model.

8. The method of claim 1, wherein the object detection model uses one or more arthropod identifying characteristics to generate the result from the object detection model that indicates that an arthropod is detected within the identification area of the at least one image.

9. The method of claim 1, further comprising:
  sending at least a portion of the at least one image captured by the electronic arthropod detection device to a server,
  wherein the server updates the object detection model based on the portion of the at least one image captured by the electronic arthropod detection device.

10. An electronic arthropod detection device, comprising:
  a camera;
  an image sensor;
  an input device;
  a memory; and
  a processor coupled to the memory, the input device, the camera and the image sensor, wherein the processor is configured with processor-executable instructions to perform operations comprising:
    receiving an indication associated with a type of arthropod to be detected via the input device;
    retrieving an object detection model from a plurality of object detection models in response to receiving the indication associated the type of arthropod to be detected;
    capturing at least one image using the camera and image sensor while scanning a surface or a subject;
    determining whether the at least one image includes a region of interest (ROI) corresponding to an arthropod;
    providing an identification area of the at least one image to the object detection model in response to determining that the at least one image includes an ROI;
    determining using the object detection model whether an arthropod is detected within the identification area of the at least one image; and
    initiating an arthropod detected procedure in response to determining using the object detection model that an arthropod is detected within the identification area of the at least one image.

11. The electronic arthropod detection device of claim 10, wherein the camera and the image sensor are included in an arthropod detection module; and
wherein the arthropod detection module is separate from the processor.

12. The electronic arthropod detection device of claim 10, wherein the image sensor is a thermal image sensor configured to capture infrared (IR) images.

13. The electronic arthropod detection device of claim 12,
wherein the processor is configured with processor-executable instructions to perform operations further comprising capturing an IR image using the thermal image sensor, and
wherein the processor is configured with processor-executable instructions to perform operations such that providing an identification area of the at least one image to the object detection model in response to determining that the at least one image includes the ROI comprises:

defining the identification area within the captured IR image; and providing the defined identification area of the captured IR image to the object detection model.

14. The electronic arthropod detection device of claim 10, wherein the image sensor is an optical image sensor.

15. The electronic arthropod detection device of claim 14, further comprising a thermal image sensor configured to capture IR images.

16. The electronic arthropod detection device of claim 15, wherein the processor is configured with processor-executable instructions to perform operations further comprising:

capturing an IR image using the thermal image sensor; and capturing an optical image using the optical image sensor;

wherein determining whether the at least one image includes the ROI comprises:

determining whether the captured IR image includes an ROI corresponding to an arthropod; and wherein the processor is configured with processor-executable instructions to perform operations such that providing an identification area of the at least one image to the object detection model in response to determining that the at least one image includes an ROI comprises:

identifying a center point of an ROI included in the captured IR image in response to determining that the captured IR image includes an ROI;

defining a search area in the captured optical image based on the center point of the ROI included in the captured IR image;

defining an identification area in the captured optical image corresponding to the defined search area; and providing the defined identification area of the captured optical image to the object detection model.

17. The electronic arthropod detection device of claim 10, further comprising:

a display;

a light emitter; and a speaker, wherein the processor is configured with processor-executable instructions to perform operations such that initiating the arthropod detected procedure in response to determining using the object detection model that an arthropod is detected within the identification area of the at least one image comprises one or more of displaying an indication on the display that an arthropod has been detected, communicating an audio indicator via the speaker corresponding to the detected arthropod, emitting light from the light emitter corresponding to the detected arthropod, displaying on the display an image of the detected arthropod, displaying on the display instructions associated with how to remove the arthropod from the subject or the surface, and displaying on the display medical follow-up information.

18. The electronic arthropod detection device of claim 10, wherein the plurality of object detection models correspond to one or more of a tick, a bedbug, a mite, lice, a flea, and a combination thereof.

* * * * *